US012675875B2

(12) United States Patent
Ovchinnikova et al.

(10) Patent No.: US 12,675,875 B2
(45) Date of Patent: Jul. 7, 2026

(54) MACHINE LEARNING ON MULTIMODAL CHEMICAL AND WHOLE SLIDE IMAGING DATA FOR PREDICTING CANCER LABELS DIRECTLY FROM TISSUE IMAGES

(71) Applicant: UT-Battelle, LLC, Oak Ridge, TN (US)

(72) Inventors: Olga S. Ovchinnikova, Knoxville, TN (US); Jacob D. Hinkle, Oak Ridge, TN (US); Inzamam Haque, Knoxville, TN (US); Debangshu Mukherjee, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 326 days.

(21) Appl. No.: 18/340,306

(22) Filed: Jun. 23, 2023

(65) Prior Publication Data

US 2024/0020833 A1     Jan. 18, 2024

Related U.S. Application Data

(60) Provisional application No. 63/355,548, filed on Jun. 24, 2022.

(51) Int. Cl.
G06T 7/00 (2017.01)
G06T 3/40 (2024.01)
(Continued)

(52) U.S. Cl.
CPC .............. G06T 7/0012 (2013.01); G06T 3/40 (2013.01); G06V 10/7715 (2022.01);
(Continued)

(58) Field of Classification Search
CPC ..... G06T 3/40; G06T 7/0012; G06T 2200/24; G06T 2207/10056; G06T 2207/20016;
(Continued)

(56) References Cited

U.S. PATENT DOCUMENTS

| | | | |
|---|---|---|---|
| 2015/0131888 A1* | 5/2015 | Caprioli | G06F 18/28 |
| | | | 382/133 |
| 2016/0110584 A1* | 4/2016 | Remiszewski | G06V 20/69 |
| | | | 382/133 |
| 2023/0284906 A1* | 9/2023 | Wang | A61B 5/0075 |

(Continued)

OTHER PUBLICATIONS

Isberg et al., "Automated Cancer Diagnostics via Analysis of Optical and Chemical Images by Deep and Shallow Learning", Metabolites 2022, 12, 455, pp. 1-15. (Year: 2022).*

(Continued)

*Primary Examiner* — Jennifer Mehmood
*Assistant Examiner* — Jose M Torres
(74) *Attorney, Agent, or Firm* — Scully, Scott, Murphy & Presser, P.C.

(57) ABSTRACT

Systems, methods and programs including machine learning techniques which can predict a spectral image directly from an optical image of a patient's tissue sample using a first model. There may be different first models for different cancers. Each first model may be trained by using a plurality of pairs of images from different samples, respectively, where each image in a respective pair may be obtained via different imaging modalities. The systems, methods and programs may also include machine learning techniques which can predict cancer labels from the predicted spectral image using a second model. There may be different second models for different cancers. Each second model may be trained using multiple spectral images and corresponding manually input cancer labels.

41 Claims, 13 Drawing Sheets
(13 of 13 Drawing Sheet(s) Filed in Color)

Sectioning
Deparaffi-
nization
α-CHCA
Application

Tumor sections
in paraffin blocks

MALDI

MALDI
(ITO coated)

High Resolution
Microscopy

α-CHCA

H&E

(51) Int. Cl.

| | |
|---|---|
| *G06V 10/77* | (2022.01) |
| *G06V 10/774* | (2022.01) |
| *G06V 20/69* | (2022.01) |
| *G16H 30/40* | (2018.01) |

(52) U.S. Cl.
CPC .......... *G06V 10/774* (2022.01); *G06V 20/698* (2022.01); *G16H 30/40* (2018.01); *G06T 2200/24* (2013.01); *G06T 2207/10056* (2013.01); *G06T 2207/20016* (2013.01); *G06T 2207/20081* (2013.01); *G06T 2207/30081* (2013.01); *G06T 2207/30088* (2013.01); *G06T 2207/30096* (2013.01); *G06T 2207/30204* (2013.01); *G06V 2201/03* (2022.01)

(58) Field of Classification Search
CPC . G06T 2207/20081; G06T 2207/30081; G06T 2207/30088; G06T 2207/30096; G06T 2207/30204; G06V 10/764; G06V 10/7715; G06V 10/774; G06V 10/82; G06V 20/695; G06V 20/698; G06V 2201/03; G16H 30/40
See application file for complete search history.

(56) References Cited

U.S. PATENT DOCUMENTS

| | | | | |
|---|---|---|---|---|
| 2023/0298169 | A1* | 9/2023 | Li | G06T 7/0012 |
| | | | | 382/128 |
| 2023/0410301 | A1* | 12/2023 | Rajagopal | A61B 5/055 |
| 2024/0242835 | A1* | 7/2024 | Giltnane | G06T 7/0012 |
| 2025/0069229 | A1* | 2/2025 | Haley | G16H 50/20 |

OTHER PUBLICATIONS

Bird et al., "Infrared micro-spectral imaging: distinction of tissue types in axillary lymph node histology", BMC Clinical Pathology 2008, 8:8, pp. 1-14. (Year: 2008).*

Lu, M. et al., "Data-efficient and weakly supervised computational pathology on whole-slide images", Nat Biomed Eng., Jun. 2021, pp. 555-570, vol. 5, No. 6.

Randall, E. et al., "Molecular Characterization of Prostate Cancer with Associated Gleason Score Using Mass Spectrometry Imaging", Mol Cancer Res, May 2019, pp. 1155-1165, vol. 17, No. 5.

Borodinov, N. et al., "Toward nanoscale molecular mass spectrometry imaging via physically constrained machine learning on co-registered multimodal data", npj Computational Materials, 2020, pp. 1-8, vol. 6, No. 83.

* cited by examiner

MACHINE LEARNING ON MULTIMODAL CHEMICAL AND WHOLE SLIDE IMAGING DATA FOR PREDICTING CANCER LABELS DIRECTLY FROM TISSUE IMAGES

CROSS-REFERENCE TO RELATED APPLICATIONS

This application claims the benefit of U.S. Provisional Application No. 63/355,548, filed on Jun. 24, 2022, which is incorporated by reference herein in its entirety.

STATEMENT REGARDING FEDERALLY SPONSORED RESEARCH OR DEVELOPMENT

This invention was made with Government support under DE-AC05-000R22725 awarded by US Department of Energy and Office of Research and Development, Veterans Health Administration, award MVP017. The Government has certain rights to this invention.

FIELD

The present application relates generally to computers and computer applications, machine learning, chemical imaging, spectrometry, and more particularly to correlative multimodal image data including spectral image data and optical image data via machine learning and predicting spectral image data from an optical image and predicting cancer labels from the predicted spectral image data.

BACKGROUND

Cancer is a leading cause of death. Cancer may be in the form of breast cancer, skin cancer, lung cancer, prostate cancer, among others. For example, according to the American Academy of Dermatology skin cancer is the most common cancer to be diagnosed in US adults with 9,500 people diagnosed every day in the United States. Between 2007 and 2011 there were roughly 4.9 million U.S. adults treated for skin cancer, for an average annual treatment cost of $8.1 billion. This represents a significant increase in number of diagnoses and cost of treatment from the previous period of 2002 to 2006, when about 3.4 million adults were treated for skin cancer each year, at an annual average treatment cost of $3.6 billion. Out of all skin cancers, melanoma is the most dangerous and the American Cancer Society estimates there will be roughly 197,700 diagnosed cases and 7,650 deaths caused by melanoma in 2022. The annual cost of treating melanoma alone is estimated at $3.3 billion. These numbers have been steadily climbing for the past 30 years even with advances in medical diagnostics and surgical techniques. Additionally, prostate cancer (PC) is the second most common cause of cancer as well as the second leading cause of cancer death among men. Approximately 1 in 8 men will be diagnosed with PC during their lifetime.

Early detection and accurate classification are essential for proper patient care and improvement in these two parameters would aid in reducing the morbidity and mortality associated with cancer as well as significantly lowering the cost of treatment.

For skin cancer, melanocytic lesions can be broadly classified into benign, atypical/dysplastic, and malignant, however, considerable histologic overlap may occur in these groups leading to discrepancies in diagnoses and management. A recent study found that board certified pathologists achieved between 62%-70% accuracy and precision in determining melanocytic lesion classes.

It is equally problematic to identify and classify metastatic PC from images.

Diagnostic shortcoming may be attributed to the difficulty in interpreting cell types directly from the hematoxylin and eosin (H&E) stained images and then assigning them to a particular class.

One known approach is to train a model using a plurality of H&E stained images, which are labeled. Once trained, a new H&E stained image may be acquired (without labeling) and the model is used to predict the cancer labels.

Spectral images are rich with spectral information which may enable to create a mapping of spatial distribution of proteins, lipids, and small molecules in tissue sections and may be used to classify lesions/tumors using chemical biomarkers. However, the time and cost to acquire and analyze spectral images may be significant. For example, the spectral images may be mass spectrometry imaging (MSI) such as Matrix Assisted Laser Desorption Ionization-Mass Spectrometry Imaging (MALDI-MSI).

Although chemical imaging modalities, such as MALDI-MSI, have shown promise for clinical use to identify chemical biomarkers with higher confidence, the time required for sample analysis and data interpretation combined with the need for expertise in both makes direct routine utilization in pathology setting not practical.

SUMMARY

Accordingly, disclosed is a method which may comprise receiving first-spatial resolution spectral images of respective training-tissue samples and receiving corresponding second-spatial resolution digital images of the training-tissue samples. Each spectral image is indicative of one or more constitutive molecular compounds of a training-tissue sample. Each pixel of the spectral image has an associated spectrum indicative of the molecular compounds' abundance at the training-tissue sample's location corresponding to the pixel of the spectral image. At least a subset of the digital images is indicative of one or more lesions of a training-tissue sample. Each pixel of the digital image has a corresponding value indicative of a lesions' abundance at the training-tissue sample's location corresponding to the pixel of the digital image. The second-spatial resolution is higher than the first-spatial resolution. The method may further comprise training a first model. The first model may be trained by transforming each second-spatial resolution digital image of the training-tissue samples into a set of image features as first abundance maps, transforming each first-spatial resolution spectral image into a set of spectral components indicating chemical components, translating either the first abundance maps or the second abundance maps to co-register, determining first model parameters which correlate the first abundance maps with second abundance maps as co-registered and storing the first model parameters as the trained first model. The chemical components include one or more molecular compounds that coexist together spatially as the second abundance maps. The method may further comprise receiving a new second-spatial resolution digital image of a tissue sample, predicted, based on the first trained model, a spectral image corresponding to the newly received digital image of the tissue sample such as in a second-spatial resolution and predicting a cancer region based on the predicted spectral image. The cancer region may be predicted for pixels of the new second-spatial resolution digital image or pixels of the predicted spectral image.

In an aspect of the disclosure, each second-spatial resolution digital image may be a hematoxylin and eosin (H&E)-stained whole slide image.

In an aspect of the disclosure, regions of pixels in at least a subset of the digital images may be pre-labeled with corresponding cancer labels indicative of the health of the training-tissue sample over the respective regions.

In an aspect of the disclosure, the transforming each second-spatial resolution digital images of the training-tissue samples into a set of image features as first abundance maps may include extracting a plurality of structural features from each second-spatial resolution digital image using deep learning feature extraction techniques and reducing the spatial and spectral dimensionality of the plurality of structural features to obtain the set of image features. For example, the reduction of the spectral dimensionality may comprise performing a linear regression.

In an aspect of the disclosure, the deep learning feature extraction model may be pre-trained. In other aspect, the method may further comprise training a deep learning feature extraction model to extract the plurality of structural features.

In an aspect of the disclosure, first-spatial resolution spectral images may be MALDI-MS images, and the mass spectra may be MALDI-MS spectra. In accordance with this aspect, the transforming each first-spatial resolution spectral image into a set of spectral components indicating chemical components, reduces the dimensionality of mass spectra to obtain the set of spectral components. The reduction may comprise PCA and the number of spectral components may be about 200 per point.

In an aspect of the disclosure, the first model may be a linear regression model.

In an aspect of the disclosure, a reduced dimensional spectral image may be initially produced and then the dimensionality may be increased by performing an inverse PCA and the spatial dimension may also be increased by upscaling.

In an aspect of the disclosure, the method may further comprise training a second model by correlating the second abundance maps with the cancer labels pre-labeled for at least a subset of first-spatial resolution spectral images.

In an aspect of the disclosure, the method may further comprise identifying a spectrum (or multiple spectra) associated with cancer based on the training and associated chemical biomarker(s).

In an aspect of the disclosure, the prediction of the cancer regions may include using the second model and labeling regions of pixels of the newly received digital image with cancer labels indicative of the health of the tissue sample over the respective regions. The predicted labels may be compared with pathologist labels.

In an aspect of the disclosure, the first model may be separately trained for different types of cancer using representative first-spatial resolution spectral images and corresponding second-spatial resolution digital images for the type of cancer. The types of cancers may include skin cancer or prostate cancer.

In an aspect of the disclosure, the translating either the first abundance maps or the second abundance maps to co-register may comprise identifying fiducial markers visible of first-spatial resolution spectral images and the corresponding second-spatial resolution digital images and translating either the first abundance maps or the second abundance maps based on the identified fiducial markers.

Also disclosed is a system which may comprise a memory, a user interface and a processor. The memory may be configured to store a first model having first model parameters. The first model parameters correlate first abundance maps with second abundance maps which are co-registered. The first abundance maps are a set of image features which are determined from second-spatial resolution digital images of training-tissues samples, respectively. Each pixel of a respective digital image has a corresponding value indicative of a lesions' abundance at the training-tissue sample's location corresponding to the pixel of the digital image. The second abundance maps are a set of spectral components indicating chemical components. The chemical components include one or more molecular compounds that coexist together spatially. The set of spectral image components may be determined from corresponding first-spatial resolution spectral images of the respective training-tissue samples. Each spectral image is indicative of one or more constitutive molecular compounds of a training-tissue sample. Each pixel of the spectral image has an associated spectrum indicative of the molecular compounds' abundance at the training-tissue sample's location corresponding to the pixel of the spectral image. The second-spatial resolution is higher than the first-spatial resolution. The user interface may be configured to enable a user to upload a second-spatial resolution digital image of a tissue sample of a patient for prediction of a spectral image corresponding to the second-spatial resolution digital image. The processor may be configured to retrieve the stored first model having first model parameters and predict the spectral image corresponding to the second-spatial resolution digital image using the first model and the first model parameters.

In an aspect of the disclosure, the predicted spectral image may be a second-spatial resolution.

In an aspect of the disclosure, the memory may be configured to further store a second model with second model parameters. The second model correlates spectral values with cancer labels. The second model parameters may be determined from pre-labeled second-spatial resolution digital images and the corresponding first-spatial resolution spectral images. The second model may be associated with the first model. The processor may be configured to predict a cancer region of pixels from the predicted spectral image using the second model with the second model parameters.

In an aspect of the disclosure, the memory may be configured to store a plurality of sets of models. Each set may comprise a first model and a second model for a specific cancer. Each first model correlates first abundance maps with second abundance maps which are co-registered and trained based on representative pairs of images for the respective specific cancer. The corresponding second model correlates spectral values with the respective specific cancer. In accordance with this aspect, the user interface may be configured to receive a selection of one set of models from among the plurality of sets of models for used in the prediction and in response to the selection, the processor may retrieve the selected set from memory.

In an aspect of the disclosure, the system may further comprise a communication interface.

In an aspect of the disclosure, the user interface may be a web portal accessible via the communication interface and the Internet and the processor and memory may be in a server and the web portal may be accessible from a terminal device. For example, the web portal may be accessible using a user identifier and a password. The memory may be configured to store patient specific information including a name, notes regarding the patient, the second-spatial resolution digital image of the tissue sample of the patient and the predicted spectral image corresponding to the second-spatial resolution digital image and cancer labels predicted from the spectral image in a patient record. The patient specific information may be only available with a user identifier and password associated with the patient specific record.

In an aspect of the disclosure, the second-spatial resolution digital image may be a hematoxylin and eosin (H&E)-stained whole slide image and the spectral image may be a mass spectral image, such as a MALDI-MS image. The mass spectra may be MALDI-MS spectra.

In an aspect of the disclosure, each first model may be a linear regression model which may predict a reduced dimensional spectral image. The dimension of the reduced dimensional spectral image may be increased, and the spatial dimension may be increased by upscaling.

In an aspect of the disclosure, the processor may be further configured to identify biomarkers based on the intensity of spectral components in the predicted spectral image, after increasing the dimension.

Also disclosed is a system which may comprise a communication interface, a processor and memory. The communication interface may be configured to receive first-spatial resolution spectral images of respective training-tissue samples and corresponding second-spatial resolution digital images of the training-tissue samples. Each spectral image is indicative of one or more constitutive molecular compounds of a training-tissue sample. Each pixel of the spectral image has an associated spectrum indicative of the molecular compounds' abundance at the training-tissue sample's location corresponding to the pixel of the spectral image. At least a subset of the digital images is indicative of one or more lesions of a training-tissue sample. Each pixel of the digital image has a corresponding value indicative of a lesions' abundance at the training-tissue sample's location corresponding to the pixel of the digital image. The second-spatial resolution is higher than the first-spatial resolution. The processor may be configured to train a first model by transforming each second-spatial resolution digital image of the training-tissue samples into a set of image features as first abundance maps, transforming each first-spatial resolution spectral image into a set of spectral components indicating chemical components, wherein the chemical components include one or more molecular compounds that coexist together spatially as second abundance maps, translating either the first abundance maps or the second abundance maps to co-register; determining first model parameters which correlate the first abundance maps with the second abundance maps as co-registered; and storing the first model parameters as the trained first model. The memory may be configured to store the trained first model. The trained first model enables prediction of a spectral image corresponding to a received new second-spatial resolution digital image of a tissue sample.

In an aspect of the disclosure, each second-spatial resolution digital image may be a hematoxylin and eosin (H&E)-stained whole slide image and each first-spatial resolution spectral image may be a MALDI-MS image, and the mass spectra may be MALDI-MS spectra.

In an aspect of the disclosure, regions of pixels may be pre-labeled with corresponding cancer labels indicative of the health of the training-tissue sample over the respective regions in at least a subset of the digital images.

In an aspect of the disclosure, the processor may extract a plurality of structural features from each second-spatial resolution digital image using deep learning feature extraction techniques to transform each second-spatial resolution digital images of the training-tissue samples into a set of image features as first abundance maps and reduce the spatial and spectral dimensionality of the plurality of structural features to obtain the set of image features.

In an aspect of the disclosure, the processor may reduce the dimensionality of mass spectra to obtain the set of spectral components to transform each first-spatial resolution spectral image into a set of spectral components indicating chemical components such as by performing PCA.

In an aspect of the disclosure, the processor may be further configured to train a second model based on the second abundance maps with the cancer labels pre-labeled for at least a subset of first-spatial resolution spectral images.

In an aspect of the disclosure, the memory may be configured to store a plurality of first models. Each first model may be separately trained by the processor for different types of cancer using representative first-spatial resolution spectral images and corresponding second-spatial resolution digital images for the type of cancer. The memory may also be configured to store a plurality of second models. Each second model is separately trained by the processor for the different types of cancer. The first model and the second model for a respective cancer form a model set.

In an aspect of the disclosure, the processor may identify fiducial markers visible in first-spatial resolution spectral images and the corresponding second-spatial resolution digital images and translate either the first abundance maps or the second abundance maps based on the identified fiducial markers to translate either the first abundance maps or the second abundance maps to co-register.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A illustrates a representation of the specimen; FIG. 4B illustrates a representation of a slide for spectral imaging (MALDI) and a slide for optical imaging; FIG. 4C illustrates a removal process for preparing the specimen for optical imaging from spectral imaging; and FIG. 4D illustrates an example of the spectrum.

FIGS. 11A, 11E and 11I are the corresponding original optical images with markings;

FIGS. 12A, 12D and 12G show an actual principal component, FIGS. 12B, 12E and H show the corresponding predicted principal component and FIGS. 12C, 12F and 12I show the actual v. predicted spectra at a specific point; FIGS. 13A and 13D are the original optical image for two specimens with markings, FIGS. 13B and 13E are the ground truths for the biomarkers and FIGS. 13C and 13F are the predicted biomarker.

DETAILED DESCRIPTION

Figure 1:
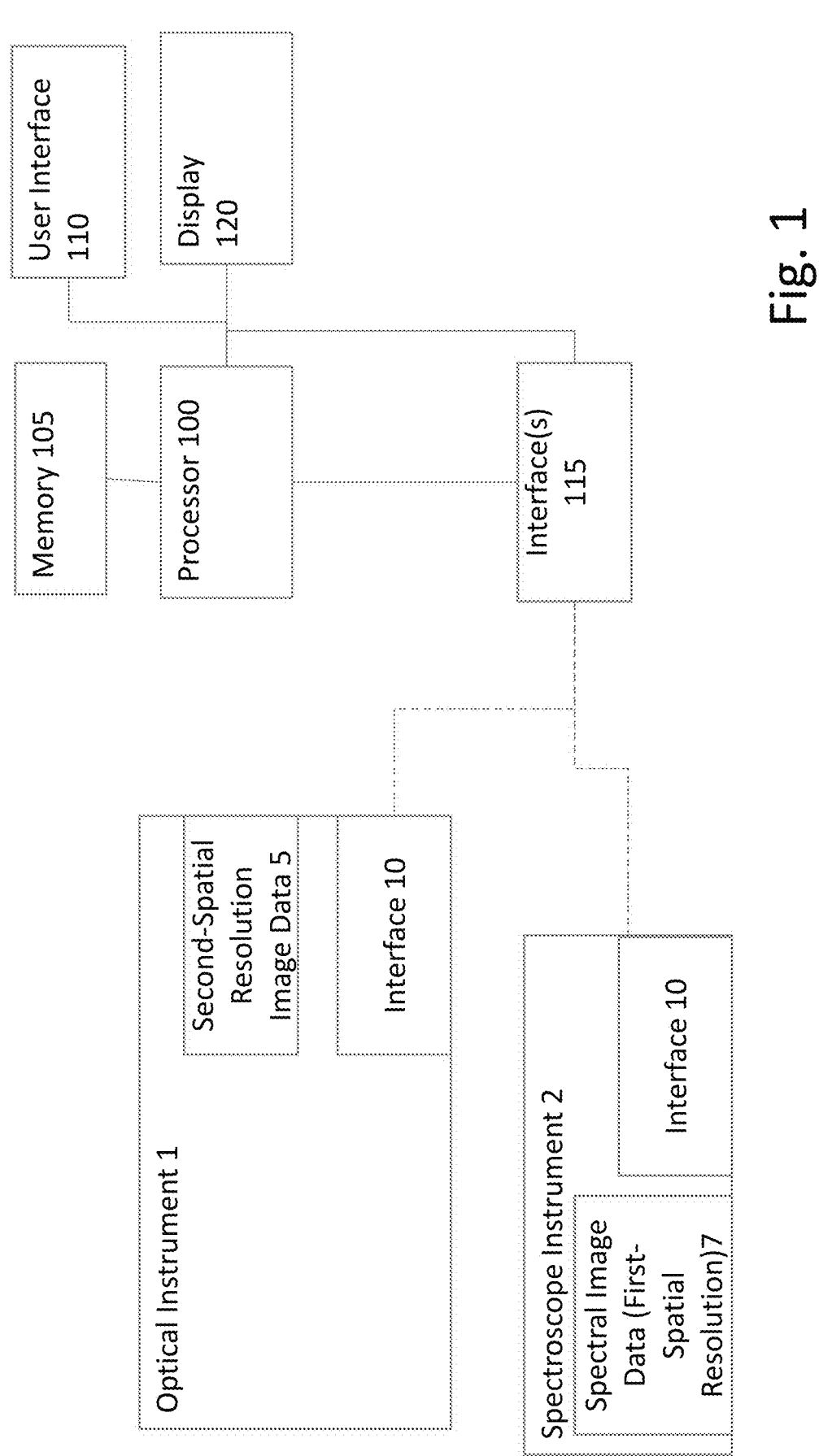
FIG. 1 illustrates an example of a system for training models in accordance with aspects of the disclosure.

Aspects of the disclosure, provide systems, methods and programs including machine learning techniques which can predict spectral image data (spectral image) directly from an optical image. This prediction may be based on a first model 605 (individually 605A, 605B, . . . for different cancers). Each first model 605 may be trained by using a plurality of pairs of images from different samples, respectively, where each image in a respective pair may be obtained via different imaging modalities. For example, one of the images in the pair is an optical image and the other image in the pair may be a spectral image. The training images may be obtained from a known patient image database or newly acquired using the instruments such as shown in FIG. 1 in a train system. While it may be helpful, training the first model 605 does not require use of manual labels.

Aspects of the disclosure, also provide systems, methods and programs including machine learning techniques which can predict cancer labels from the predicted spectral image data (spectral image) using a second model 610 (individually 610A, 610B, . . . for different cancers). The second model 610 may be trained using multiple spectral images and manually input cancer labels such as being superposed on the optical images, respectively.

FIG. 1 illustrates an example of a system for training models in accordance with aspects of the disclosure (machine learning system). As shown, the system has two instruments: an optical instrument 1 (optical microscope) and a spectroscope instrument 2 (Spectrometer). The optical microscope 1 may be an optical bright field microscopy. In some aspects of the disclosure, the optical image is obtained in a single shot. However, in other aspects, multiple images may be acquired and stitched. For example, the optical microscope may be a high-resolution stitched optical bright field microscopy. Each optical image may have one or more lesions. Lesions used herein may be tumor, mass, abscess, wound, ulcer, etc. Each pixel has a value, such as a color value, indicative of an abundance of a lesion at the particular position. No abundance is where the lesion is not present. In other aspects, one of the optical images used for training may not have a lesion.

The spectroscope 2 may be an instrument that can acquire chemical images (spectral images). A chemical image may be indicative of one or more molecular compounds of a specimen (sample of a patient). Each pixel has an associated spectrum indicating an abundance of one or more molecular compound's location.

For example, the spectral image may be a mass spectral image (MSI). The spectroscope may be capable of acquiring matrix-assisted laser desorption/ionization (MALDI) images, such as ionization-time-of-flight (MALDI-TOF) or time-of-flight secondary ion mass spectrometry (ToF-SIMS) imaging. For example, the spectroscope may be a 9.4T MADLI Fourier-transform ion cyclotron resonance (FTICR) MS such as from Bruker.

The spectral image is not limited to mass spectrum, but can include other spectral images providing chemical information such as fluorescent imaging, infra-red imaging, Raman, electron backscatter diffraction (EBSD) and electron energy loss spectroscopy (EELS).

Each instrument 1, 2 has its own storage (memory) for storing the respective image data as it is acquired prior to transmission. The optical image data 5 and the spectral image data 7 may have two different spatial resolutions, where the spatial resolution of the optical image is higher than the spatial resolution of the spectral image. The higher spatial resolution data is also referred to herein as second-spatial resolution and the lower spatial resolution data is also referred to herein as first-spatial resolution. The spectral image data Z is saved in the spectroscope 2 and the image data 5 is saved in the optical microscope 1.

Each instrument 1, 2 may also comprise an interface 10. This interface 10 may be a communication interface such as a USB port. A data acquisition card (DAQ) such as from National Instruments may be connected to the interface 10. In an aspect of the disclosure, the interface 10 may be a wireless or wired network interface.

Each instrument 1, 2 may also comprise instrument specific components needed to acquire the images.

Although shown as two different instruments 1, 2, in some aspects of the disclosure the same instrument may be used for acquiring both optical image data and spectral image data.

The system may also comprise a processor 100. The processor 100 may be one or more central processing unit(s) CPUs. The processor 100 may be one or more graphics processing unit GPUs. In other aspects of the disclosure, the processor 100 may be a microcontroller or microprocessor or any other processing hardware such as a field programmable gate array (FPGA) or an application specific integrated circuit (ASIC). In an aspect of the disclosure, the processor 100 may be configured to execute one or more programs stored in a memory 105 to execute the functionality described herein. The memory 105 may be, for example, RAM, persistent storage or removable storage. The memory 105 may be any piece of hardware that is capable of storing information, such as, for example without limitation, data, programs, instructions, program code, and/or other suitable information, either on a temporary basis and/or a permanent basis.

The memory 105 stores patient information such as the name, age, clinical outcomes, diagnosis, images (both optical and spectral) acquired from the instruments 1, 2 or obtained from a known database. The memory 105 may also include the predicted spectral image(s) (in both different spatial and spectral resolutions) and predicted labels for new patients (associated with personal information). "New Patients" is used to define patients whose data was not used for training (validation or testing) of either the first model 605 or the second model 610. Training of the model(s) includes training, validation and testing (prior to deployment).

One CPU or GPU may execute the functionality described herein or multiple CPUs or GPUs may collectively execute the functionality described herein. For example, the CPUs or GPUs may execute some of the functionality in parallel to speed up the training process. For example, one CPU or GPU may process the optical image data to define features for registration and a second CPU or GPU may process the spectral image data to define features for registration. Another CPU or GPU may co-register the features and learn the first model parameters. Additionally, one CPU or GPU may execute the training for the first model 605 and another CPU or GPU may execute the training for the second model.

The processor 100 may be connected to the instruments 1, 2 via an interface 115, respectively and the DAQ. One of the interfaces may also be a USB to connect the DAQ. In an aspect of the disclosure, the interface 115 may be a wireless or wired network interface.

In an aspect of the disclosure, the processor 100 is installed as part of a server and remote from the instruments 1, 2. For example, the processor 100 may be connected to the instruments via a LAN or WLAN (and via the Internet).

The system may comprise a user interface 110. In an aspect of the disclosure, the user interface 110 may interact with the processor 100 (such as a server) via the Internet and may be remote from the processor 100 (such as a web portal). For example, the user interface 110 may be in a terminal such as a portable terminal like a mobile telephone or a laptop and as described above, the processor 100 may be installed as part of a server system. The user interface 110 may be displayed via a web browser or be part of an application installable on the terminal. The display 120 may also be remote from the processor 100 such as installed in the same terminal as the user interface 110.

The user interface 110 may be used by an operator to identify which pairs of images (optical and spectral) are to be used for training the first model 605. Additionally, the user interface 110 may be used to add patient information including clinical outcomes associated with the images and doctor or radiologist notes (pathologist commentary) and other patient records. Since the memory 105 (and processor 100) has or has access to private patient information, the web portal may be password protected (require input of a user identifier or a user password). If there are more than one patient record, different patient records may be associated with different user identifiers (and passwords).

The first model 605 and the second model 610 may be trained for a specific cancer such as skin cancer and prostate cancer, etc . . . . Thus, the model parameters for the first model 605 may be different for a model used for predicting the spectral image for skin cancer 605A v. prostate cancer 605B.

The models are trained using a plurality of pairs of images. The number of pairs may be as little as a handful and as many as 100. However, the more pairs are used for training, the longer the training may take due to the time to acquire the spectral images. In an aspect of the disclosure, the pairs of images should be representative images (of the cancer for prediction). For example, there may be different classes relevant to a type of cancer such as classes of melanocytic lesions including (I) benign nevus (including blue, Spitz and spindle cell nevi), (II) atypia/dysplastic (III) malignant melanoma (in situ and invasive). Therefore, the pairs of images should include at least one pair from each class.

Figure 4:
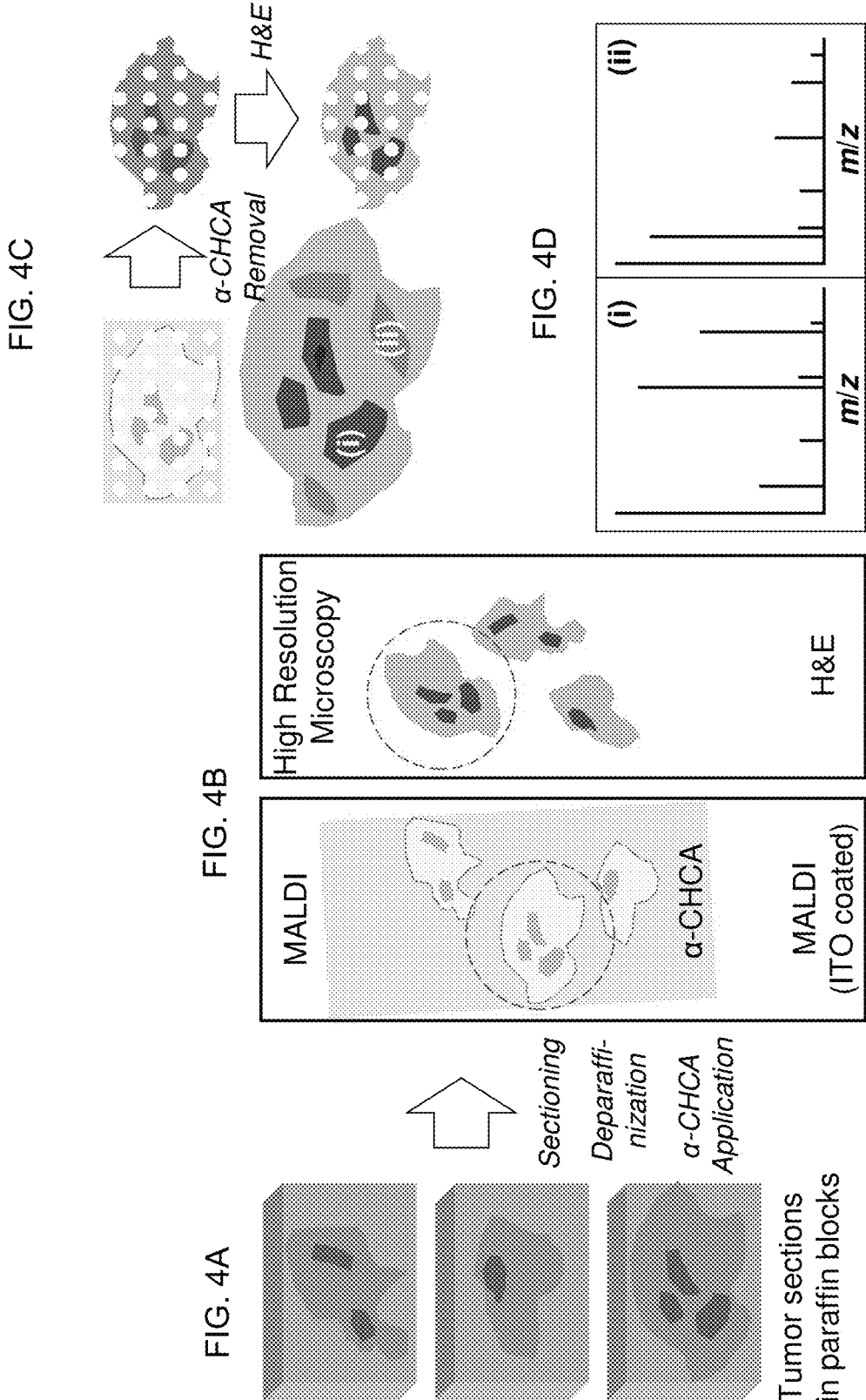
FIGS. 4A-4D illustrate an example of preparing the specimen (samples) for imaging and the two imaging techniques and correlations, where
Figure 5:
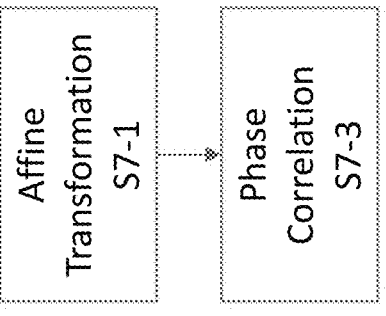
FIG. 5 illustrates an example of the co-registration method.

FIGS. 4A-4C illustrate an example of preparing the samples for imaging for training. For example, FIG. 4A shows a representation of three different tumor sections in paraffin blocks.

A tumor section can be deparaffinized using xylene incubation and be sectioned into thin layers using a microtome. For example, the layers may be 5-10 μm. In an aspect of the disclosure, the same layer may be used for both optical and spectral imaging. In other aspects, serial layers can be isolated and used for separate microscope glass slides, one of which may be conductively coated for spectral imaging as such, but not limited to MSI e.g., with indium tin oxide, ITO, while the other, intended for the optical microscopy, may be stained using H&E such as shown in FIG. 4B. When serial layers are used, prior to co-registration, transformation may be needed for alignment and correlation.

The section(s) intended for spectral imaging such as MSI may be further treated for antigen retrieval in a decloaking chamber. The slide may be uniformly sprayed with a trypsin solution for enzymatic digestion using a robotic platform. After a few hours following the trypsin application, a solution of α-cyano-4-hydroxycinnamic acid (CHCA) can be applied in the same way using the robotic spotting platform such as shown in FIG. 4B.

In an aspect of the disclosure, to help with co-registration of serial layers, after the spectral image is obtained, the remaining matrix can be washed off and the slide can be H&E stained such as shown in FIG. 4C. H&E-stained slides may be imaged and used for co-registration of the features.

In an aspect of the disclosure, although not needed for training the first model, H&E-stained slides can be analyzed by a trained pathologist who can mark and classify the tumor areas, which may be used for training the second model. In an aspect of the disclosure, the marking or additional marking may also be used for helping the co-registration such as fiducial markers. The dots on FIG. 4B represent fiducial markers.

In an aspect of the disclosure, slides may have multiple regions of interest and be used to generate multiple pairs of images for training. In some aspect of the disclosure, the pathologist marking may be used for identifying the ROI and training targets. FIG. 4D illustrates two example points within the images and corresponding spectral data (i) and (ii).

Figure 2:
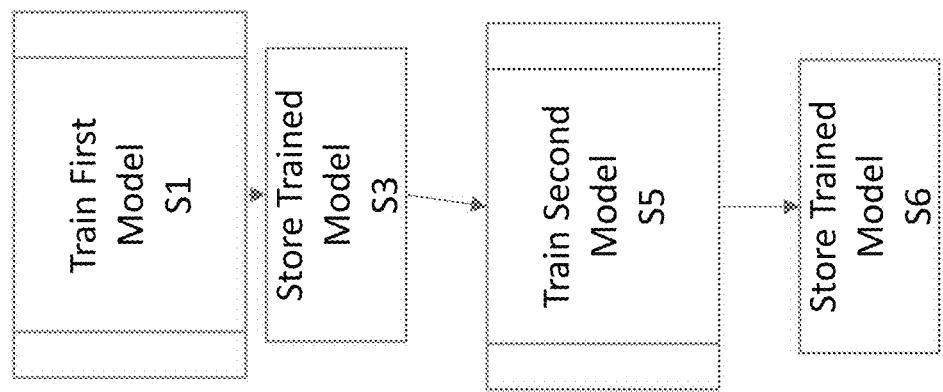
FIG. 2 illustrates an example of a method for training the models in accordance with aspects of the disclosure.

FIG. 2 illustrates an example of a method in accordance with aspects of the disclosure. At S1, the first model 605 is trained. In an aspect of the disclosure, the first model 605 may be a regression model. The regression model may be a linear regression model and the model parameters may include "M" and "B", where M is the slope and "B" is the offset.

Figure 3:
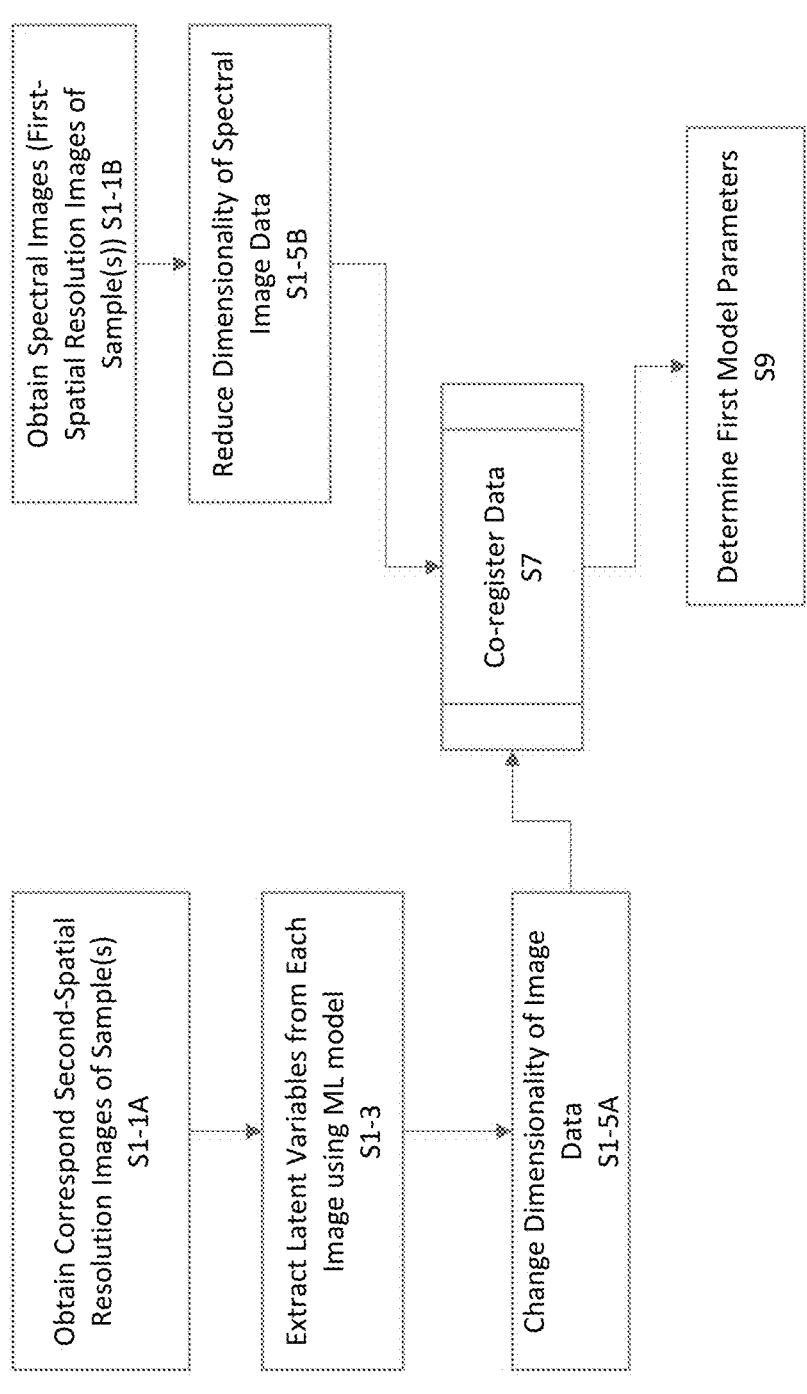
FIG. 3 illustrates an example of a method for training the first model in accordance with aspects of the disclosure.

FIG. 3 illustrates an example of a method for training the first model 605 in accordance with aspects of the disclosure. At S1-1B, each spectral image used for training may be acquired. In an aspect of the disclosure, the user, using the user interface 110 (web portal) may upload a pre-acquired spectral image (data) into the memory 105 for the processor 100 to access. In other aspects, the spectral images may be obtained from a known database of images. The spectral data may have a first spatial resolution. The spatial resolution may be based on the type of spectral image such as type of MS or IR or fluorescent image or defined based on the instrument 2 or cancer screening. For example, the pixel size may be 120 μm. In other aspects, the pixel size may be 50 μm. the spectral image may be newly acquired under the control of the processor 100.

The spectral image may be received in different formats (also depending on the instrument 2). For example, the spectral image may be in an imzML format, which is a common data format for a spectral image such as MS (and a different format than the optical image data). However, imzML files are typically large such as in a range of a couple of hundred gigabytes. In an aspect of the disclosure, the data may be converted into another format for further processing.

Moreover, since the optical image has a different format, it is preferable to convert into a uniform format for both. In an aspect of the disclosure, a Hierarchical Data File (HDF) format may be used, e.g., HDF5. HDF5 enables faster processing and storage. Each file contains a large number of spectra such as mass spectra (MS), which enables the production of an ion image of a whole slide and spectra from a single or multiple spatial coordinates.

Figure 8:
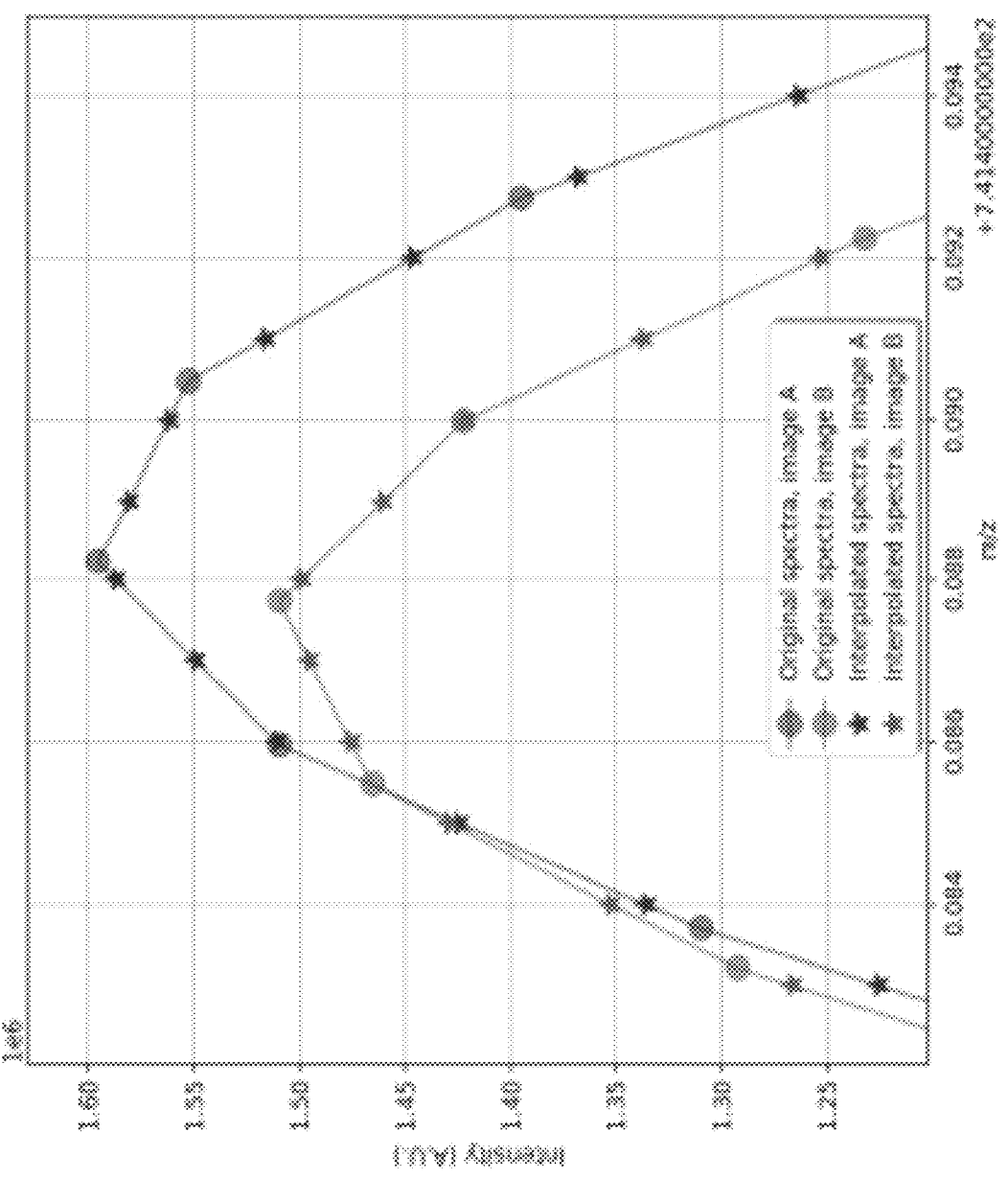
FIG. 8 illustrates an example of two spectral image datasets before and after interpolation in accordance with aspects of the disclosure.

Each different spectral image may have a different number of spectral points at different coordinates. Accordingly, to have the same spectral axis across images and points, in an aspect of the disclosure, prior to format conversion, spectral intensity values may need to be interpolated for some points and images. FIG. 8 illustrates an example of an interpolation for two different MS images. The circles represent the original spectra associated with images A and B. As can be seen, the points do not align vertically. FIG. 8 shows a slight difference in the spectra points. In FIG. 8, the stars represent the interpolated values. As can be seen, these values are vertically aligned.

The range and step size of the interpolation may be based on the spectra of interest. For example, the interpolation for a MS may be for m/z values ranging from 100 to 1,000, with a step size of 0.001. These values are for descriptive purposes only. After interpolation, the file may be converted into the HDF5 format.

At S1-1A, each corresponding optical image used for training is acquired. In an aspect of the disclosure, the user, using the user interface 110 (web portal) may upload the optical image (data) into the memory 105 for the processor 100 to access. In other aspects, the images may be obtained from a known database of images. The optical image data may have a second resolution, e.g., high resolution. As noted above, the optical image may be acquired from the same or different slide of the tumor. The optical image may be acquired under the control of the processor 100.

The optical image may be received in different formats (also depending on the instrument 1). For example, the high-resolution whole slide H&E image (tissue) may be provided in a Carl Zeiss CZI format (a proprietary format). In an aspect of the disclosure, for faster processing and storing a correlation, the optical image data may also be converted into HDF5.

In an aspect of the disclosure, the optical image data may be normalized prior to further processing. For example, each optical image may be normalized to have a zero mean and a unit standard derivation in each color channel. In some aspects, the normalization may occur prior to the file format conversion.

At S1-3, the processor 100 may extract latent variables (features) from each of the normalized optical images (H&E images). The latent variables may be extracted using a machine-learned model (deep learning feature extraction model). For example, the processor 100 may implement a deep neural network. In some aspects, the deep neural network is pre-trained for extracting features from H&E images. For example, a pretrained ResNet-50 model may be used. ResNet-50 is a convolutional neural network that is 50 layers deep (48 convolutional, one MaxPool layer and one average pool layer). The model may be pre-trained with images from ImageNet and a Pytorch deep learning framework.

In other aspects of the disclosure, instead of using a pre-train model (DNN), the processor 100 can train a DNN using imaged selected by a user via the user interface 110 or newly acquired optical images since optical images are easily acquired (quickly acquired).

However, given the size of the optical images such as H&E images, in an aspect of the disclosure, the images may be processed in patches. The patches may be a preset size. In an aspect of the disclosure, the user may set the size of the patches using the user interface 110. For example, the patch size may be 512×512.

In some aspects of the disclosure, prior to feeding the images (patches) to the feature extractor, a grid artifact removal process may be executed. For example, a halo may be added around the patches. This halo may be a preset number of pixels, such as, but not limited to 256.

For each image, the DNN extracts a certain number of features (channels). For example, the DNN (feature extractor) may identify a number of channels (data) given that data is extract between in the third layer (onward). The number of channels may be, for example, 3 to 1024. However, since the ResNet-50 also has an average pool layer, the spatial dimension (output by the DNN) may be reduced. For example, the spatial dimension may be reduced by 16 times using the average pool layer.

Prior to or during the feature extraction (from the optical image(s)), the processor 100 also reduces the dimensionality of the spectral image data in each spectral image at S1-5B (spectral dimensional). This is because the interpolated spectral image data is too large to practically process. For example, for a MS image, at each point in each image, there are about 900,000 spectral channels (at thousands of points). In some aspects of the disclosure, principal component analysis (PCA) may be used to reduce the dimensionality of each individual spectra. Reducing the dimensionality of the spectral image data is not limited to PCA and other known dimensional reduction techniques may be used, such as, but not limited to non-negative matrix factorization (NMF) and one or more clustering algorithms.

A collection of the spectral images may be used to determine the principal components. For example, certain of the spectral images may be used for training and validation and certain of the spectral images may be held out for testing (after training and validation).

In some aspects, incremental PCA from a scikit-learn library may be used to fit the training (validation and testing) in memory 105 and for a faster convergence.

In an aspect of the disclosure, PCA may be used to determine the number of components for further processing and correlation. For example, the determination may be based on a cumulative explained variance. In an aspect of the disclosure, there may be a user-defined cumulative explained variance threshold for determining the number. For example, the threshold may be set at 95%. In other aspects, the threshold may be higher such as 97% or 98%.

FIGS. 9B-9F illustrate the first five principal components of an example spectral image and in this case a MS image (of the tissue specimen). A bar below the figures is given showing intensity values in arbitrary units for the five components. Although the components show hints of cancerous regions, no single component can clearly identify cancerous regions. FIG. 9G illustrates a cumulative explained variance achieved by the components. The highest explained variance is achieved with a minimum of 200 components as seen from FIG. 9G.

Figures 9A, 9B, 9C, 9D, 9E, 9F, 9G:
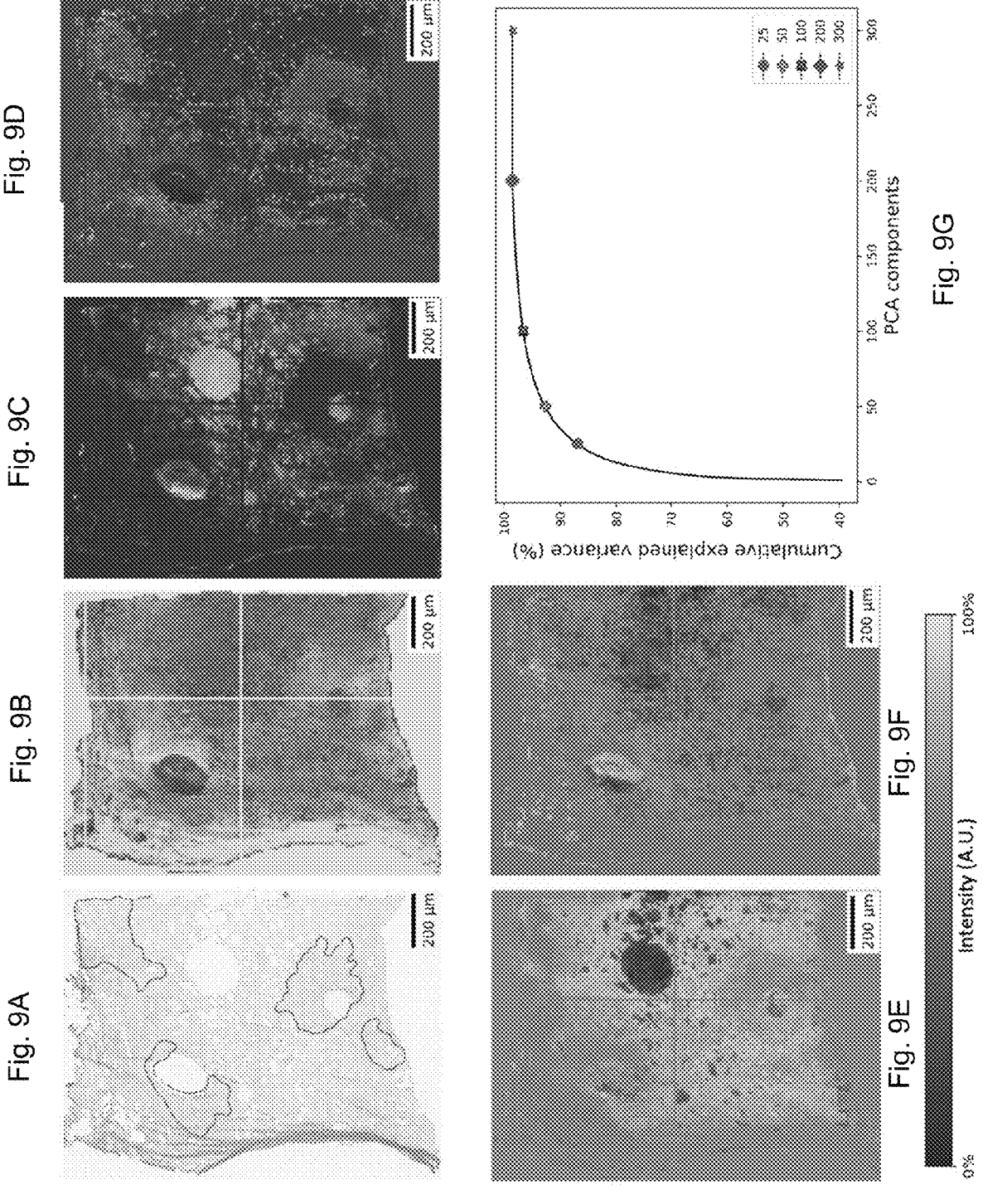
FIG. 9A illustrates an example of an optical image with markings in accordance with aspects of the disclosure.
FIGS. 9B-9F illustrate the first five principal components for a corresponding spectral image in accordance with aspects of the disclosure and FIG. 9G illustrates a relationship between the number of principal components and the cumulative explained variance for the corresponding spectral image.

The different shaped points on the graph in FIG. 9G represent values of 25, 50, 100, 200, and 300. The values of the cumulative explained variance for 25, 50, 100, 200, and 300 principal components are respectively 86.68%, 92.71%, 97.08%, 98.51%, and 98.50% (for this image). Principal components value greater than 200 do not improve results for this image. These 200 components explained 98.51% of the variability in the data with the first three components combined explaining 67% variability for this image. FIG. 9A shows the corresponding optical image (with markings).

At S1-5A, the processor 100 may adjust the dimensionality of the extracted features to match with the spatial dimension of the principal components from the PCA (or reduced spectral components in another manner as described above). In some aspects of the disclosure, the extracted features (optical features) may re-gridded. Considering the extracted optical features as the source dataset and the reduced spectral components as the target dataset, two strategies may be used: downscaling and upscaling. Downscaling is used when the target shape is smaller than the source shape. If the source shape is an integer multiple of the target shape, average pooling may be performed. Otherwise, Gaussian blurring may be performed followed by subsampling.

Once the spatial dimensions of the two datasets are the same (processed optical image data as described above and processed spectral image data as described above), the processor 100 reduces the spectral dimension of the optical image dataset. For example, the processor may perform a linear regression to reduce the dimensionality (number of channels) to the same as the number of principal components. For example, the number of spectral channels in the optical image dataset may be 1024. Other dimension reduction techniques may also be used such as, but not limited to PCA. The technique may be based on the number of channels and the processor type (processing power).

Afterwards, the processor 100 co-registers the data at S7. The reduced dataset for the optical image is also referred to as first abundance maps (which is a set of image features). The set has multiple image features per point The reduced dataset for the spectral image is also referred to as second abundance maps (which is a set of spectral components). The second abundance maps indicate the chemical components (one or more molecular compounds that coexist together spatially). The set has multiple spectral components at each corresponding point.

At S7-1, the processor 100 may perform an affine transformation. This may be particularly helpful where the optical image and the spectral image was acquired using different slices of the specimen. This is because the x and y dimensional of the specimen may be different in the difference slices. Additionally, when two different instruments are used, the specimen position(s) may be different. The images may also be distorted based on a specific acquisition technique. The affine transformation may also be used due to image resolution and focus. The affine transformation may scale, reflect, rotate or apply a shear mapping to one of the datasets to create an alignment or matching such that the two closely match on a pixel to pixel basis. In an aspect of the disclosure, only one of the datasets may be translated. For example, the spectral dataset may be translated to match the spatial dataset (or vice versa).

In some aspects of the disclosure, pre-existing points visible in both images may be used for alignment. However, in other aspects of the disclosure, fiduciary markings may also be used such as a dot or dashed lines.

Figures 10A, 10B:
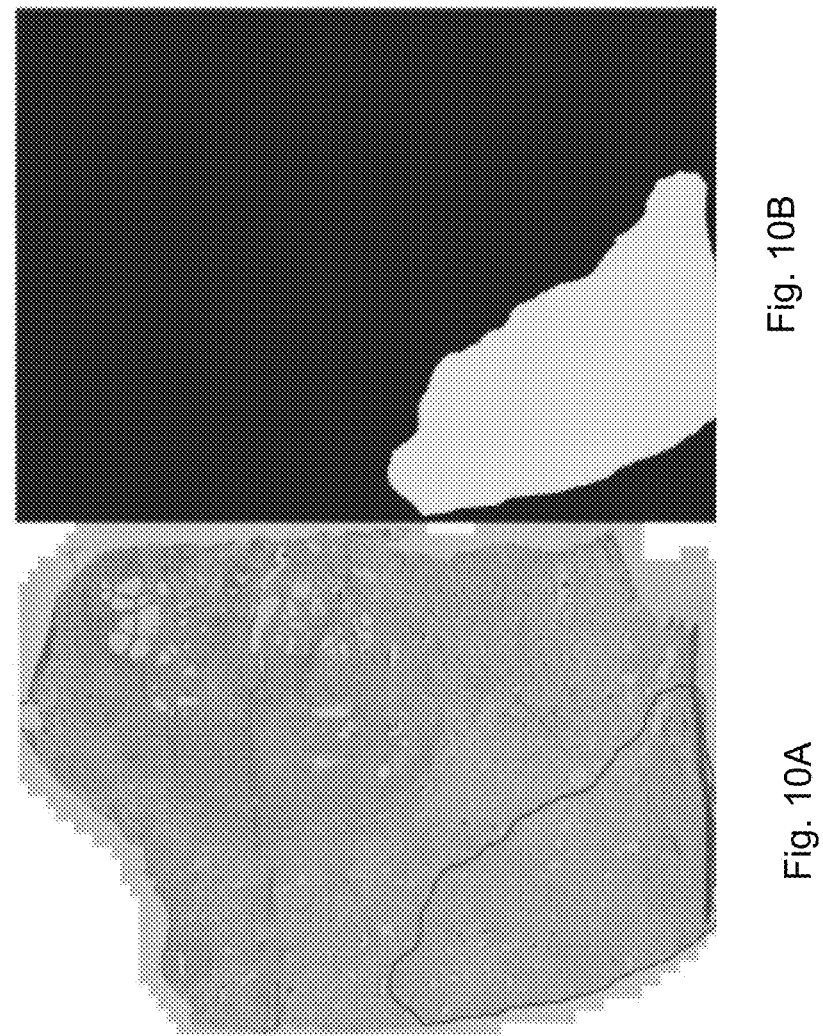
FIG. 10A illustrates another example of an optical image with markings in accordance with aspects of the disclosure and FIG. 10B illustrates a corresponding binary mask.

In yet another aspect of the disclosure, a binary mask may be used for alignment purposes (although may not be required if there are other sources for alignment). In an aspect of the disclosure, the binary mask may be based on pathologist annotations. In some aspects, the pathologists may mark a corresponding lower-resolution optical image such as the H&E image, respectively, for each optical image in the training. A binary mask is extracted from the contours for both cancer and noncancer regions as well as non-tissue background of each image. FIG. 10A illustrates an example of a low-resolution optical image with a pathologist annotations and FIG. 10B illustrates the corresponding extracted binary mask. Since the masks are acquired from the lower-resolution optical image, prior to use to co-register, a binary mask, corresponding to each higher-resolution optical image may be upscaled to correspond to the spatial resolution. In other aspects, the low-resolution masks may be directly used to match without upscaling to the higher spatial resolution. However, the binary masks may need to be scaled to have the same spatial resolution as the spectral dataset. The binary mask image may be more computation friendly than the original H & E image based on the lower resolution. Thus, the comparison may be between the spectral dataset as the input and the binary mask image as the output (or vice versa). The affine transformations transforms the input and iteratively adjusts the transformation parameters (which may be a matrix), until the input matches closely with the output.

At S7-3, the processor 100 may perform a phase correlation. The phase correlation is an efficient subpixel image translation registration by cross-correlation. In some aspects, the correlation may be used from a scikit-image library.

Once the reduced datasets are co-registered, the processor 100 may determine model parameters for the first model 605 at S9 (first model parameters). As described above, the first model 605 may be a linear regression model. However, the first model 605 is not limited to linear regression. For example, a deep convolution neural network may also be used (to correlate the abundance maps). Here the model parameters would be the weights in the network.

A subset of the co-registered image datasets may be used for training (including validation) and certain co-registered image datasets may be used for testing. Cross validation may be used. For example, a 5-fold cross validation may be used. Model parameters determined using the co-registered image datasets reserved for trained/validation may be tested on the withheld datasets to see how well the spectral data is predicted using the model parameters (and linear regression) and compared with the known spectral data from the withheld datasets (predicted v. actual). Other cross validations may be used such as, but not limited to a 10-fold cross validation.

In some aspects of the disclosure, an Adam optimizer with a learning rate of 0.1 may be used to converge to the model parameters. Once converged, the processor 100 stores the model parameters in the memory 105 at S3 as the trained model.

S1-1A-S9 may be repeated for each different cancer such as breast, skin, prostate, lung, etc. The memory 105 may store a trained first model 605 for different cancers, e.g., one for skin 605A, one or prostate 605B, one for lung, one for breast, etc. . . .

Referring back to FIG. 2, at S5, the processor may train the second model 610 to predict the cancer labels from the spectral image(s) predicted using the first model, e.g., learn the model parameters for the second model. The model parameters may be weights and bias. The bias may be a single number and the number of weights is equal to the number of input features.

Once again, there may be dedicated model parameters for the different cancers and thus S5 may be executed for each cancer and associated with the corresponding first model (e.g., 605A associate with 610A and 605B associated with 610B etc. . . . ).

In some aspects of the disclosure, the second model 610 may be a logit model also known as a logistic regression. Logistic regression is for classification. The second model 610 may be trained using the same spectral image(s) identified above (input by the user). In some aspects, the dimensionally downsized dataset may be used, e.g., components from PCA. For example, 200 components may be used. The number of spectral components is not limited to 200 and may be determined in a similar manner as described above.

A subset of the spectral image data may be used for training (and validation and subsequently testing. A similar cross validation may be used as described above such as, but not limited to a 5-fold cross validation. In some aspects of the disclosure, the pathologist annotations may be used as the input labels. As noted above, for skin cancer, the pathologist annotations may include the class. In other aspects, the binary masks extracted above may be used as the labels.

The processor 100 may implement a stochastic gradient Descent (SGD) classifier. A SGD classifier may have an equivalent estimator in the Scikit-learn API. The estimator may implement regularized linear models. In an aspect of the disclosure, the estimation may use one or more learning techniques. For example, a "log" loss technique may be used. In other aspects, a "squared" error or penalty may be used.

The "log" loss gives logistic regression, a probabilistic classifier. A predefined regularization parameter may be used. For example, a regularization parameter of 0.01 may be used with an adaptive learning rate starting from 0.01.

In an aspect of the disclosure, there may be a class imbalance in labels. This may be a direct result from there being less cancerous regions in the image than non-cancerous regions (two class where cancerous is one class and non-cancerous is another). In order to solve this problem, a "balanced" class weight fit preset which uses the values of labels to automatically adjust weights inversely proportional to class frequencies in the input data may be used for training. After training, the model parameters may be tested using on holdout image data to check performance. For example, the classification labels predicted for the spectral image data may be compared with the actual classification labels by the pathologist.

At S6, the processor 100 stores the model parameters in the memory 105 as the trained second model. In some aspects, the trained second model for a specific cancer may be associated with the trained first model 605 such that if the corresponding first model 605 is selected, the trained second model 610 is automatically selected for use.

Figure 6:
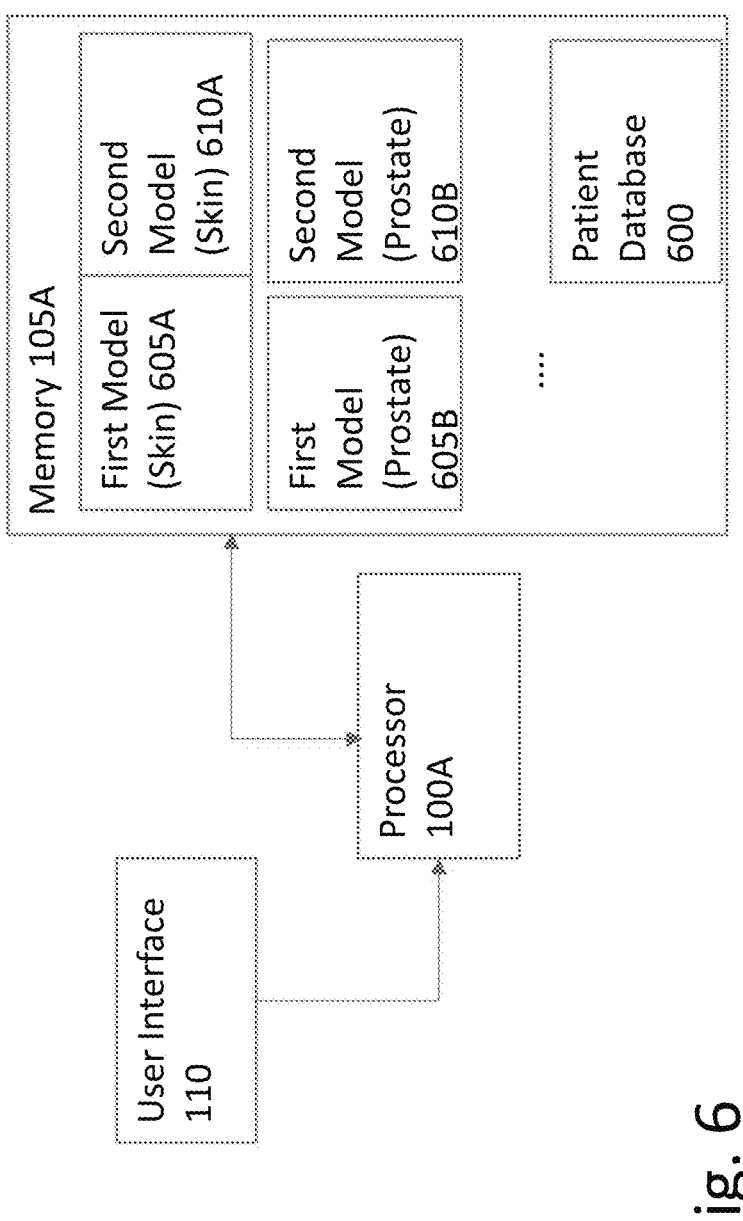
FIG. 6 illustrates an example of a system for predicting spectral image data from optical image data of a target in accordance with aspects of the disclosure.

FIG. 6 illustrates an example of a system for predicting spectral image data from optical image of a target in accordance with aspects of the disclosure. The system comprises a processor 100A, memory 105A and a user interface 110. The processor 100A may be the same or a different processor 100 from the processor used in training (validation and testing) of the first model(s) 605 and the second model(s) 610. This processor 100A may be included in a server which can only be accessed via a web portal and via the Internet. The user interface 110 may be included in a terminal. The terminal may comprise a display and a communication interface such as a wired or wireless communication interface. The user interface 110 may be in the form of a graphic user interface associated with the web portal. For example, a web portal may be displayed on a display of the terminal. A splash page for the web portal may display an area for a user to login with credentials such as a user identifier and a password.

The memory 105A may include all prior trained first model(s) 605 (stored in S3) and corresponding second model(s) 610 (stored in S6). The memory 105A may also have a restricted patient database 600. The database 600 may contain patient data from multiple doctors, radiologists and pathologists. The user identifier and password may be associated with a subset of the patients records such that patient confidentiality is maintained. Additionally, for security, data transferred between the server (processor 100A) and terminal (user interface 110) may be encrypted. The patient database 600 may include as described above personal information of the patient such as name, age . . . etc., patient diagnoses, treatment options, outcomes, any notes from the doctors, radiologists, and pathologists. The patient database 600 may also include the optical images, any spectral images of the respective patients, predicted spectral images and predicted labels.

Figure 7:
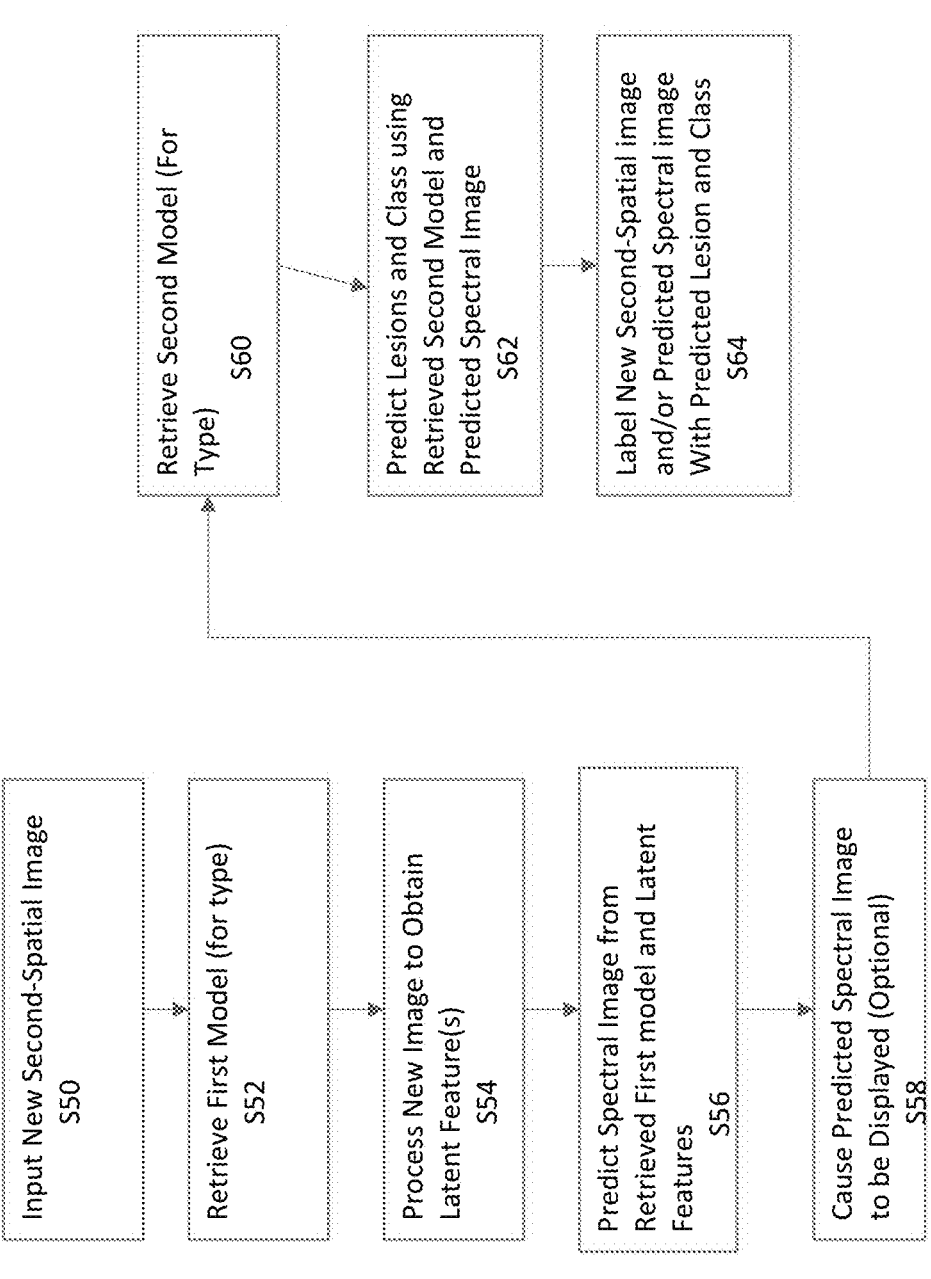
FIG. 7 illustrates an example of a method for predicting the spectral image data and labelling in accordance with aspects of the disclosure.

FIG. 7 illustrates an example of a method for predicting the spectral image data and labeling in accordance with aspects of the disclosure. At S50, after login into the system, the user may input a new optical image into the database. For example, the user may create a new patient record by inputting personal information and other relevant information. The processor 100A may also prompt the user to upload a new optical image for the new patient. In other aspects, the optical image may be for a patient already in the system. In this aspect of the disclosure, the processor 100A may prompt the user to identify the pre-existing patient and subsequently prompt the user to upload a new optical image. The optical image may be acquired from the same instrument 1 used for training the models. In other aspects, a different instrument (but the same type) may be used. In other aspects, in response to the user inputting a patient's name, the processor 100A may instruct an optical microscope to acquire an image.

In an aspect of the disclosure, the processor 100A may cause the user interface 110 to display a list of available first models 605 (and the corresponding second model 610). In other aspects, the list may only include the available first models 605 (with listing the second model 610). The user may select one of the available first models 605 displayed on the display. In some aspects, the list may display the model parameters. In other aspects, the list may have an icon associated with a model name for the user to select. In other aspects, the user interface 110 may have a prompt to input a name of the first model 605.

In response to receiving a selection of the first model 605 (from the user interface 110), the processor 100A retrieves the selected model in S52.

At S54, the processor 100A processes the new optical image to obtain a set number of latent features. The processing is the same as described above in S1-3 and S1-5A with respect to the optical images for training/validation/testing of the first model(s) 605.

At S56, the processor 100A predicts spectral image data associated with the latent features using the first model retrieved in S52. For example, the processor 100A uses the linear regression model with the model parameters to predict a set number of reduced spectral components (set number of principal components) of the spectral image. In some aspects, the processor 100A may execute a reverse dimensional reduction method to obtain a spectral image at a full spectral resolution. For example, a reverse PCA may be used. Additionally, at S56, the processor 100A may upscale the spectral image to obtain the same spatial resolution as the new optical image. In some aspects, linear interpolation may be used.

Advantageously, by using the selected first model, a spectral image may be obtained, which is rich in chemical information, from the optical image, which is quicker and easier to obtain as opposed to having to acquire the actual spectral image such as a MS.

In some aspects, optionally, the processor 100A at S58 may cause the predicted spectral image to be displayed at the terminal (on the user interface 110). The displayed spectral image may have a full spectral resolution or be based on the set reduced spectral components (set number of principal components). The image may have the same spatial resolution as the new optical image or reduced spatial resolution. In an aspect of the disclosure, instead of or in addition to the spectral image, a graph showing the intensity of each spectral value within the spectral image may be shown such as for the reduced spectral components (set number of principal components).

These intensity graphs enable the discovery of chemical-specific biomarkers which can be linked to a cancer labeling (once the labels are predicted).

At S60, the processor 100A retrieves the second model 610 associated with the selected first model 605 from memory 105A. In other aspects, the user may directly select the second model 610 in a similar manner as described above.

At S62, the processor 100A predicts the locations of the lesion and class using the retrieved second model 610 and the predicted spectral image data. The prediction may be on a pixel basis where the pixel has a spatial resolution of the first-spatial resolution. In particular, since the predicted spectral image may have the same number of spectral components as the spectral image data used for training/validation and testing, the processor 100A may use as input to the second model 610 same number spectral components at each point and the second model 610 outputs the classification (distinguishes between cancer and non-cancer). This prediction is repeated for each point. However, in other aspects, since the spectral image data may be upscaled, the pixel may have a second-spatial resolution.

At S64, the processor 100A may add the predicted labels to the predicted spectral image. For example, based on the classification, the processor 100A may identify the boundary of the lesion on the predicted spectral image as superpose the boundary on the spectral image. Additionally, within the predicted location of the lesion, the processor 100A may superpose the determination (e.g., cancer or not cancer, and class). For example, for skin cancer, the class may be benign nevus, atypia/dysplastic or malignant melanoma. When there are more than two classes, multinomial logistic regression may be used.

The processor 100A may also identify the spectral value with high intensities (greater than a threshold) when the pixel(s) are identified as cancerous, e.g., chemicals specific biomarkers.

The boundary and labels may also be added to the optical image (which was used as the basis for the prediction). However, since the spatial resolution of the optical image and the predicted spectral image may be different, as noted above, upscaling may be needed to place the boundary. The upscaling may include a linear interpolation.

The automated labeling from the predicted spectral image provides a means for having a "second opinion" for pathologists. This may lead to better patient outcomes and reduced treatment costs. Earlier and more accurate diagnoses may allow less invasive treatments and may improve patient outcomes, while lowering the overall costs of the treatment including leading to less invasive procedures.

In an aspect of the disclosure, where the predicted labeling differs from a pathologists initial labeling of the same image, the pathologist may recheck the image for confirmation, order an additional image of the same tumor of a different slice (if available) or request an additional biopsy.

In an aspect of the disclosure, the system may provide automated therapeutic recommendations to doctors based on the labeling and predicted spectral image.

Experiment and Testing

Aspects of the disclosure of predicting cancer using models to predict cancer from the optical image via a predicted spectral image was tested and compared with single imaging modes of prediction. The models in accordance with aspects of the disclosure were trained (validated and tested) using 5 pairs of optical/spectral images.

The 5 spectral images, and in this case, mass spectrometry data consisted of human prostate tissue specimens that were cryosectioned and imaged at a pixel size of 120 μm using a 9.4 T SolariX XR FT ICR MS (Bruker Daltonics, Billerica, MA).

The corresponding optical image (H&E whole slide images) were acquired using an Axio Imager M1 microscope scanner system for telepathology at 40× magnification.

For the "optical image only mode prediction", each optical image was processed in a similar manner as described above in S1-1A, S1-3, S1-5A to obtain a reduced optical image dataset.

For the "spectral image only mode prediction", each spectral image (MS image) was processed in a similar manner as described above in S1-1B, S1-5B to obtain a reduced spectral image dataset (set number of principal components).

For the "multi-image mode prediction" using both the optical image and the spectral image (MS image), the two datasets (abundance maps) were co-registered in S7 and the first model parameters were determined in S9.

A 5-fold cross-validation was used during training (validation) for all the logistic regression models. For each fold, total pixels of the four preprocessed tissue images, excluding the holdout image for testing, are shuffled, and divided into 80%-20% for training and validation, respectively.

For the "optical image only mode prediction", the second model (logistic regression model) was trained using the regridded deep H&E features to predict cancerous regions and to compare performance. The same extracted binary masks (e.g., FIG. 10B) that was used for the MSI data training were used as the labels for logistic regression. Scikit-learn's SGD classifier that implements regularized linear models with stochastic gradient descent (SGD) learning was used for the training. "log" loss that gives logistic regression, a probabilistic classifier was used. A regularization parameter of 0.001 was used with an adaptive learning rate starting from 0.001. Similar to the MSI logistic regression training, a "balanced" class weight fit preset which uses the values of labels to automatically adjust weights inversely proportional to class frequencies in the input data, essentially removing class imbalance of the training data was used. After training, the model was tested on a holdout image to evaluate performance.

For the "multi-image mode prediction", the first model parameters (linear regression) were determined using 5-fold cross validation with Adam optimizer with a learning rate of 0.1 has been used, and the convergence took 20000 iterations.

Based on apriori knowledge of certain potentially relevant spectra, the upper range of m/z values was increased from 1,000 to 1,500 since an original interpolation accounted for 100-1,000 m/z values.

200 principal components (predicted) were converted into 1,500,000 spectral components using an inverse PCA transformation from scikit-learn library to do the transformation. A certain portion of the full spectral resolution was further examined and compared with the ground truth (Actual MSI image data).

Chemical biomarkers were identified from the ground truth MSI that best captured the cancerous regions of the tissue specimens and then observed the predicted MSI.

As expected, the chemical rich MS image data (spectral image only mode prediction) has better prediction than optical image only mode prediction: 85% of the pixels v. 80% of the pixels based on the holdout image from each validation. Multi-image mode prediction achieved an 80% accuracy of the pixels (based on 200 principal components). Less than 200 principal components have a reduced accuracy; however, more than 200 do not appear to improve the accuracy.

Figures 11A, 11B, 11C, 11D, 11E, 11F, 11G, 11H, 11I, 11J, 11K, 11L:
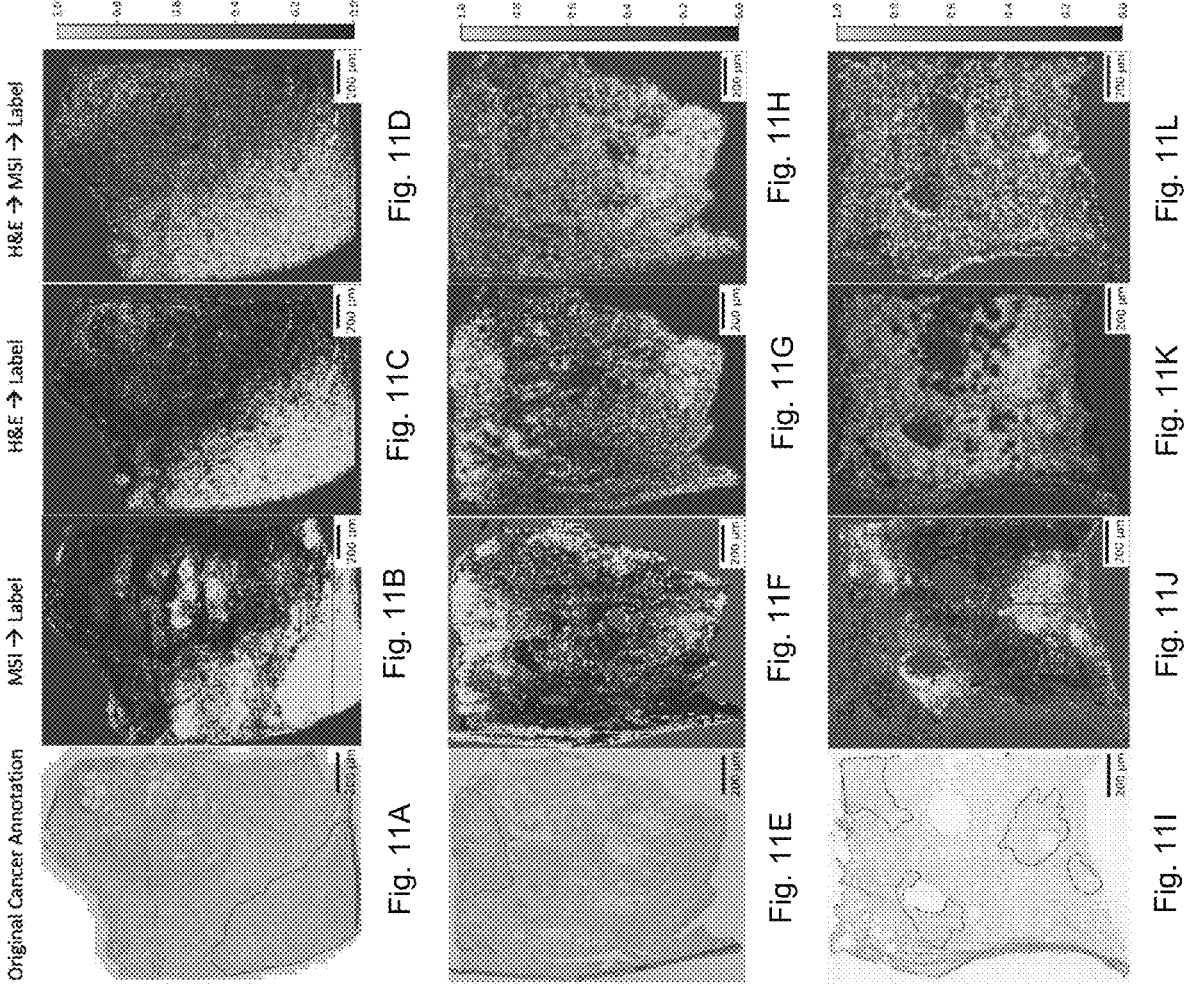
FIGS. 11A-11L illustrate a comparison between three cancer label predictive methods (modes): spectral image only mode prediction (FIGS. 11B, 11F and 11J); optical image only mode prediction (FIGS. 11C, 11G and 11F); and multi-image mode prediction in accordance with aspects of the disclosure (FIGS. 11D, 11H and 11L) and where

FIGS. 11A-11L illustrate a comparison of the three different prediction modes for three different images (three tissue specimens of the five obtained). FIGS. 11A, 11E and 11I illustrate the original optical image (H&E image) with marking (cancer annotation). FIGS. 11B, 11F and 11J illustrate the predicted cancer regions for the spectral image only mode prediction (MSI->Label). FIGS. 11C, 11G and 11K illustrate the predicted cancer regions for the optical image only mode prediction (H&E->Label). FIGS. 11D, 11H and 11L illustrate the predicted cancer regions for the multi-image mode prediction (H&E->MSI->Label). All the predictions in these figures are achieved using the second model (logistic regression). The colorbar represents the probability of cancer annotation for each row. Row one shows good agreement between MSI (FIG. 11B) and H&E (FIG. 11C), with a possible false positive region that is not labeled in the H&E (FIG. 11C) or H&E to MSI (FIG. 11D) predicted components (the cancerous regions were revealed with for all three predictions).

In row two, MSI (FIG. 11F) and H&E (FIG. 11G) perform well, but H&E to MSI (FIG. 11H) underperforms. In row three, MSI (FIG. 11J) significantly outperforms H&E (FIG. 11K), and H&E to MSI (FIG. 11L) partially recovers some of that performance.

Some secondary regions are revealed with the MSI to label prediction. When looking at the prediction for the second tissue specimen (row 2) directly from H&E in FIG.

11G, the secondary region seen with MSI prediction is revealed more. Interestingly, this region is revealed even more when predicted from predicted MSI components as seen in FIG. 11H. These secondary regions can be random noise or actual cancerous regions which can be missing in the original annotation and are subject to further validation.

Label prediction directly from MSI is best for the third tissue specimen as seen in FIG. 11J. But two primary regions are missing in the other two predictions for this specimen as shown in FIGS. 11K and 11L.

The results demonstrate the import of using the MSI data for prediction and the benefit of obtaining the MSI data without having to take the time to acquire that MS image which is typically unavailable in a normal pathology lab. Additionally, since the models were trained only with five optical and/or five spectral images, it is expected that the accuracy of the prediction will improve with addition training images and more variability in the training data, especially for the multi-image mode prediction. Even with the small sample set, the prediction as described herein gives reasonable results to show that prostate cancer (and others) could be diagnosed accurately with correlating MSI and H&E data using the first model 605 and labeling using the second model 610. The results demonstrate a correlation between features visible on the optical image and the chemical information present in the spectral image.

Figures 12A, 12B, 12C, 12D, 12E, 12F, 12G, 12H, 12I:
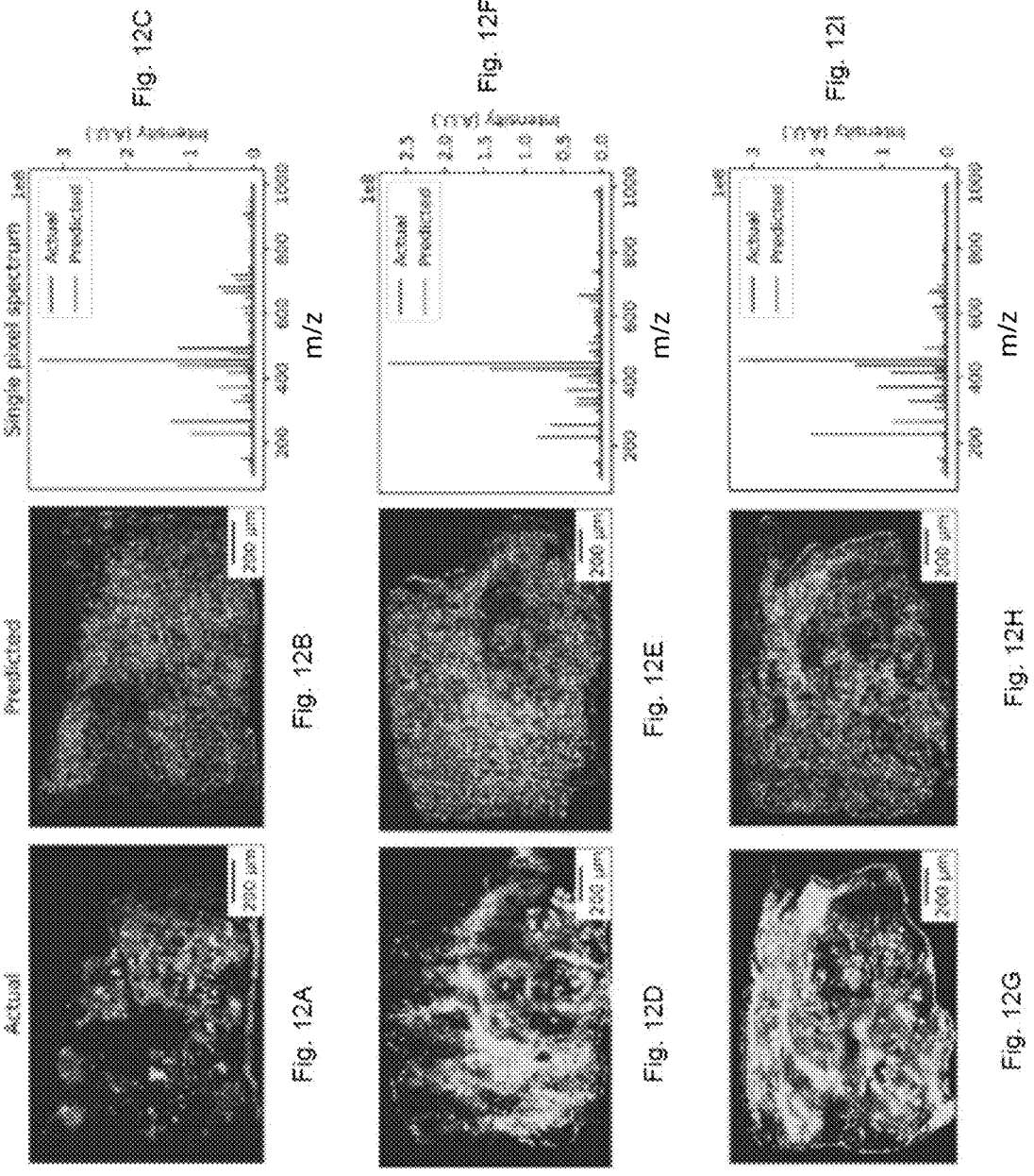
FIGS. 12A-12I illustrate a comparison between an actual and predicted component of spectrum, where

FIGS. 12A-12I illustrate a comparison of the ground truth (actual) versus the prediction of the spectral image (MSI) from the optical image (H&E) (e.g., processed as described above). FIGS. 12A, 12D and 12G show the actual first principal component for three different tissue specimens. The images in FIG. 12A-12I are rotated 90 degrees with respect to the images in FIG. 11A-11L. FIGS. 12B, 12E and 12H show the predicted first principal component. For the three tissue specimens, spectra of a single pixel (red star marker) from the cancerous region are shown both for actual and predicted in FIG. 12C, FIG. 12F, and FIG. 12I. Negative values of the predicted spectra are clipped. The same range of intensity values in arbitrary units was used in these figures for each predicted image. Similar patterns can be seen in the predicted MSI directly from H&E corresponding to the actual MSI images, with row 2 having slightly better prediction compared to the other two rows. The accompanying predicted spectra for each row is clearly able to capture most of the m/z peaks in the actual spectra, although there is an intensity mismatch between the actual and predicted spectra. The predicted is in red and the actual is in blue.

Figures 13A, 13B, 13C, 13D, 13E, 13F:
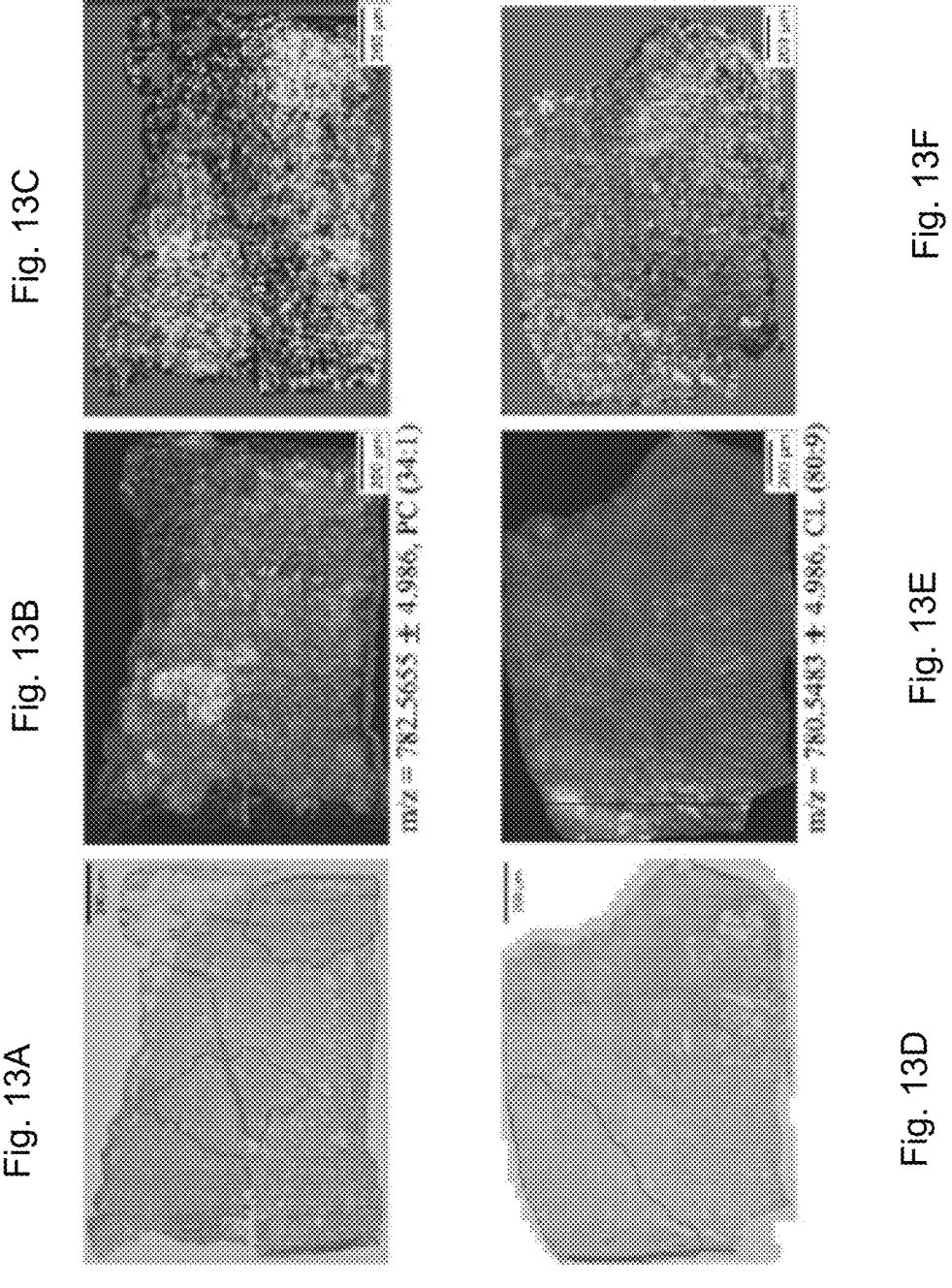
FIGS. 13A-13F illustrate a comparison of two biomarkers from actual and predicted spectra including showing the optical image with markings, where

FIGS. 13A-13F illustrate a comparison of cancer region predictions as described herein from H&E images via predicted MS image data and ground truth and identified biomarkers. FIGS. 13A and 13D are the original H&E images with markers (annotations) for two different tissue specimens (of the five). FIG. 13D is the same image in FIG. 11A but rotated 90 degrees. FIG. 13B illustrates the ground truth MSI of the first tissue specimen for m/z 782.5655 which is identified as phosphatidylcholine PC(34:1) ($\Delta$ppm=1.93). FIG. 13C illustrates the predicted MSI of the first tissue specimen for the same m/z as ground truth from the optical image. FIG. 13E illustrates the ground truth MSI of the second tissue specimen for m/z 780.5483 which is identified as cardiolipin CL(80:9) ($\Delta$ppm=0.18). FIG. 13F illustrates the predicted MSI of the second tissue specimen for the same m/z as ground truth from the optical image.

As can be seen in FIG. 13B, the biomarker identified reveals a cancerous region (which coincided with one of the pre-marked regions). The predicted MSI for this biomarker appears to identify cancerous regions in FIG. 13C, when compared with the original tissue annotation in FIG. 13A. Interestingly, in FIG. 13B, the ground truth MSI captures one of the cancerous regions but misses the other completely whereas the predicted image in FIG. 13C captures the region missing in the ground truth.

The second biomarker, cardiolipin, provided similar results as seen with the first tissue specimen. Like the original MSI, the predicted MSI images for these two m/z values also show the same secondary predicted cancer regions that were missing in the original annotation. FIGS. 13A-13F show that in addition to labeling prostate cancer, aspects of the disclosure also provide useful additional information in the form of predicted chemical information. Since the cancer predictions are made directly from inferred chemical signatures, the results are inherently explainable by the chemical signatures at each point that were predicted from patterns detected on the H&E images.

The second tissue specimen also achieved satisfactory detection results. The cancerous regions can be identified by both the ground truth (FIG. 13E) and the predicted (FIG. 13F).

The secondary regions may be errors due to random noise or cancerous regions which were missing in the original pathology annotation. Additional validation of these secondary regions would be useful, for example, using immunohistochemistry (IHC) imaging.

Provisional application Ser. No. 63/355,548 describes additional examples of the spectral images such as the MALDI MSI images. This description is incorporated by reference herein.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10% or ±20%, or any point therein. For example, the term about when used for a measurement in mm, may include+/0.1, 0.2, 0.3, etc., where the difference between the stated number may be larger when the state number is larger. For example, about 1.5 may include 1.2-1.8, where about 20, may include 19.0-21.0.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

References in the specification to "one aspect", "certain aspects", "some aspects" or "an aspect", indicate that the aspect(s) described may include a particular feature or characteristic, but every aspect may not necessarily include the particular feature, structure, or characteristic. Moreover, such phrases are not necessarily referring to the same aspect. Further, when a particular feature, structure, or characteristic is described in connection with an aspect, it is submitted that it is within the knowledge of one skilled in the art to affect such feature, structure, or characteristic in connection with other aspects whether or not explicitly described.

As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually. For example, a single FPGA may be used or multiple FPGAs may be used to achieve the functions, features or instructions described herein. For example, multiple processors may allow load balancing. In a further example, a server (also known as remote, or cloud) processor may accomplish some or all functionality on behalf of a client processor.

The terminology used herein is for the purpose of describing particular aspects only and is not intended to be limiting the scope of the disclosure and is not intended to be exhaustive. Many modifications and variations will be apparent to those of ordinary skill in the art without departing from the scope and spirit of the disclosure.

What is claimed is:

1. A method comprising:
receiving first-spatial resolution spectral images of respective training-tissue samples, wherein each spectral image is indicative of one or more constitutive molecular compounds of a training-tissue sample, and wherein each pixel of the spectral image has an associated spectrum indicative of the molecular compounds' abundance at the training-tissue sample's location corresponding to the pixel of the spectral image;
receiving corresponding second-spatial resolution digital images of the training-tissue samples, wherein at least a subset of the digital images is indicative of one or more lesions of a training-tissue sample, wherein each pixel of the digital image has a corresponding value indicative of a lesions' abundance at the training-tissue sample's location corresponding to the pixel of the digital image, and wherein the second-spatial resolution is higher than the first-spatial resolution;
training a first model by
transforming each second-spatial resolution digital image of the training-tissue samples into a set of image features as first abundance maps,
transforming each first-spatial resolution spectral image into a set of spectral components indicating chemical components, wherein the chemical components include one or more molecular compounds that coexist together spatially as second abundance maps,
translating either the first abundance maps or the second abundance maps to co-register; and
determining first model parameters which correlate the first abundance maps with the second abundance maps as co-registered and storing the first model parameters as the trained first model;
receiving a new second-spatial resolution digital image of a tissue sample;
predicting, based on the trained first model, a second-spatial resolution spectral image corresponding to the new second-spatial resolution digital image of the tissue sample; and
predicting a cancer region of pixels in the new second-spatial resolution digital image based on the predicted second-spatial resolution spectral image.

2. The method of claim 1, wherein each second-spatial resolution digital image is a hematoxylin and eosin (H&E)-stained whole slide image.

3. The method of claim 2, wherein in the at least a subset of the digital images, regions of pixels are pre-labeled with corresponding cancer labels indicative of a health of the training-tissue sample over the respective regions.

4. The method of claim 3, further comprising training a second model by correlating the second abundance maps with the cancer labels pre-labeled for the at least a subset of digital images.

5. The method of claim 4, further comprising identifying spectra associated with cancer based on the training and associated chemical biomarkers.

6. The method of claim 5, wherein the prediction of the cancer regions includes using the second model and labeling regions of pixels of the new second-spatial resolution digital image with cancer labels indicative of a health of the tissue sample over the respective regions.

7. The method of claim 1, wherein the transforming each second-spatial resolution digital images of the training-tissue samples into a set of image features as first abundance maps, includes:
extracting a plurality of structural features from each second-spatial resolution digital image using deep learning feature extraction techniques; and
reducing a spatial and spectral dimensionality of the plurality of structural features to obtain the set of image features.

8. The method of claim 7, further comprising training a deep learning feature extraction model to extract the plurality of structural features.

9. The method of claim 7, wherein the reducing of the spectral dimensionality comprises performing linear regression.

10. The method of claim 1, wherein the first-spatial resolution spectral images are MALDI-MS images, and the mass spectra are MALDI-MS spectra.

11. The method of claim 10, wherein transforming each first-spatial resolution spectral image into a set of spectral components indicating chemical components, reduces a dimensionality of mass spectra to obtain the set of spectral components.

12. The method of claim 11, wherein the reducing comprises performing principal component analysis (PCA).

13. The method of claim 12, wherein a number of spectral components in the set is about 200, per point.

14. The method of claim 1, wherein the first model is a linear regression model.

15. The method of claim 14, wherein the predicting, based on the trained first model, the second-spatial resolution spectral image corresponding to the newly received digital image of the tissue sample, comprises predicting a reduced dimensional spectral image and increasing the dimensionality by performing an inverse principal component analysis and increasing a spatial dimensionality by upscaling.

16. The method of claim 1, wherein the first model is separately trained for different types of cancer using representative first-spatial resolution spectral images and corresponding second-spatial resolution digital images for the type of cancer.

17. The method of claim 16, wherein the types of cancers include skin cancer or prostate cancer.

18. The method of claim 1, wherein the translating either the first abundance maps or the second abundance maps to co-register comprises identifying fiducial markers visible of first-spatial resolution spectral images and the corresponding second-spatial resolution digital images and translating either the first abundance maps or the second abundance maps based on the identified fiducial markers.

19. A system comprising:
a memory configured to store a first model having first model parameters,
the first model parameters correlate first abundance maps with second abundance maps which are co-registered, the first abundance maps are a set of image features which are determined from second-spatial resolution digital images of training-tissues samples, respectively, wherein each pixel of a respective digital image has a corresponding value indicative of a lesions' abundance at the training-tissue sample's location corresponding to the pixel of the digital image and the second abundance maps are a set of spectral components indicating chemical components, wherein the chemical components include one or more molecular compounds that coexist together spatially, the set of spectral image components being determined from corresponding first-spatial resolution spectral images of the respective training-tissue samples, wherein each spectral image is indicative of one or more constitutive molecular compounds of a training-tissue sample, and wherein each pixel of the spectral image has an associated spectrum indicative of the molecular compounds' abundance at the training-tissue sample's location corresponding to the pixel of the spectral image, the second-spatial resolution is higher than the first-spatial resolution;

a user interface configured to enable a user to upload a second-spatial resolution digital image of a tissue sample of a patient for prediction of a spectral image corresponding to the second-spatial resolution digital image;

a processor configured to retrieve the stored first model having first model parameters and predict the spectral image corresponding to the second-spatial resolution digital image using the first model and the first model parameters.

20. The system of claim 19, wherein the predicted spectral image has a second-spatial resolution.

21. The system of claim 19, wherein the memory is further configured to store a second model with second model parameters, the second model correlates spectral values with cancer labels, the second model parameters being determined from pre-labeled second-spatial resolution digital images and the corresponding first-spatial resolution spectral images, the second model being associated with the first model, and wherein the processor is configured to predict a cancer region of pixels from the predicted spectral image using the second model with the second model parameters.

22. The system of claim 21, wherein the memory comprises a plurality of sets of models, each set comprising a first model and a second model for a specific cancer, each first model correlates first abundance maps with second abundance maps which are co-registered and trained based on representative pairs of images for the respective specific cancer and the corresponding second model correlates spectral values with the respective specific cancer.

23. The system of claim 22, wherein the user interface is configured to receive a selection of one set of models from among the plurality of sets of models for use in the prediction and in response to the selection, the processor is configured to retrieve the selected set from memory.

24. The system of claim 22, wherein each first model is a linear regression model.

25. The system of claim 24, wherein each linear regression model predicts a reduced dimensional spectral image and wherein the dimension of the reduced dimensional spectral image is increased, and a spatial dimension is increased by upscaling.

26. The system of claim 25, wherein the processor is further configured to identify biomarkers based on an intensity of spectral components in the predicted spectral image, after increasing the dimension.

27. The system of claim 19, further comprising a communication interface and wherein the user interface is a web portal accessible via the communication interface and the Internet.

28. The system of claim 27, wherein the processor and the memory are in a server and the web portal is accessible from a terminal device.

29. The system of claim 28, wherein the web portal is accessible using a user identifier and a password and wherein the memory is configured to store patient specific information in a patient specific record including a name, notes regarding the patient, the second-spatial resolution digital image of the tissue sample of the patient and the predicted spectral image corresponding to the second-spatial resolution digital image and cancer labels predicted from the spectral image in a patient record, and wherein the patient specific information is only available with a user identifier and password associated with the patient specific record.

30. The system of claim 19, wherein the second-spatial resolution digital image is a hematoxylin and eosin (H&E)-stained whole slide image and the spectral image is a mass spectral image.

31. The system of claim 30, wherein the mass spectral image is a MALDI-MS image, and the mass spectra are MALDI-MS spectra.

32. A system comprising:

a communication interface configured to receive:

first-spatial resolution spectral images of respective training-tissue samples, wherein each spectral image is indicative of one or more constitutive molecular compounds of a training-tissue sample, and wherein each pixel of the spectral image has an associated spectrum indicative of the molecular compounds' abundance at the training-tissue sample's location corresponding to the pixel of the spectral image; and corresponding second-spatial resolution digital images of the training- tissue samples, wherein at least a subset of the digital images is indicative of one or more lesions of a training-tissue sample, wherein each pixel of the digital image has a corresponding value indicative of a lesions' abundance at the training-tissue sample's location corresponding to the pixel of the digital image, and wherein the second-spatial resolution is higher than the first-spatial resolution, a processor configured to train a first model by:

transforming each second-spatial resolution digital image of the training-tissue samples into a set of image features as first abundance maps, transforming each first-spatial resolution spectral image into a set of spectral components indicating chemical components, wherein the chemical components include one or more molecular compounds that coexist together spatially as second abundance maps, translating either the first abundance maps or the second abundance maps to co-register;

determining first model parameters which correlate the first abundance maps with the second abundance maps as co-registered; and storing the first model parameters as the trained first model, a memory configured to store the trained first model, wherein the trained first model enables prediction of a spectral image corresponding to a received new second-spatial resolution digital image of a tissue sample.

33. The system of claim 32, wherein each second-spatial resolution digital image is a hematoxylin and eosin (H&E)-stained whole slide image and each first-spatial resolution spectral image is a MALDI-MS image, and the mass spectra are MALDI-MS spectra.

34. The system of claim 33, wherein regions of pixels are pre-labeled with corresponding cancer labels indicative of a health of the training-tissue sample over the respective regions in the at least a subset of the digital images.

35. The system of claim 34, wherein the processor is further configured to train a second model based on the second abundance maps with the cancer labels pre-labeled for the at least a subset of the digital images.

36. The system of claim 35, wherein the memory stores a plurality of first models, each first model being separately trained by the processor for different types of cancer using representative first-spatial resolution spectral images and corresponding second-spatial resolution digital images for the type of cancer.

37. The system of claim 36, wherein the memory stores a plurality of second models, each second model being separately trained by the processor for the different types of cancer, wherein the first model and the second model for a respective cancer form a model set.

38. The system of claim 33, wherein in the transforming each second-spatial resolution digital images of the training-tissue samples into a set of image features as first abundance maps, the processor is configured to perform:

extracting a plurality of structural features from each second-spatial resolution digital image using deep learning feature extraction techniques; and reducing a dimensionality of the plurality of structural features to obtain the set of image features.

39. The system of claim 38, wherein in the transforming each first-spatial resolution spectral image into a set of spectral components indicating chemical components, the processor reduces a dimensionality of mass spectra to obtain the set of spectral components.

40. The system of claim 39, wherein the reduction comprises performing principal component analysis (PCA).

41. The system of claim 32, wherein in the translating either the first abundance maps or the second abundance maps to co-register, the processor is configured to identify fiducial markers visible of first-spatial resolution spectral images and the corresponding second-spatial resolution digital images and translate either the first abundance maps or the second abundance maps based on the identified fiducial markers.

* * * * *